US009944886B2

(12) United States Patent
Hitchcock et al.

(10) Patent No.: US 9,944,886 B2
(45) Date of Patent: *Apr. 17, 2018

(54) COATED MICROCAPSULES

(71) Applicant: Noxell Corporation, Hunt Valley, MD (US)

(72) Inventors: James Paul Hitchcock, Leeds (GB); Elaine Alice Marie Baxter, Twickenham (GB); Simon Richard Biggs, Chelmer (AU); Olivier Jean Cayre, Thurlstone (GB); Zoë Dyter, Newcastle Upon Tyne (GB); Lynette Anne Makins Holland, Abbots Langley (GB); Madhuri Jayant Khanolkar, Singapore (SG); Raul Rodrigo Gomez, Brussels (BE); Alison Louise Tasker, Toowong (AU); David William York, Newcastle Upon Tyne (GB)

(73) Assignee: Noxell Corporation, Hunt Valley, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/971,645

(22) Filed: Dec. 16, 2015

(65) Prior Publication Data

US 2016/0177221 A1 Jun. 23, 2016

Related U.S. Application Data

(60) Provisional application No. 62/092,613, filed on Dec. 16, 2014.

(51) Int. Cl.
*C11B 9/00* (2006.01)
*C23C 18/16* (2006.01)
(Continued)

(52) U.S. Cl.
CPC ............ *C11B 9/00* (2013.01); *A01N 25/28* (2013.01); *A23L 27/72* (2016.08); *B01J 13/22* (2013.01);
(Continued)

(58) Field of Classification Search
CPC .......................................... C11B 9/00
(Continued)

(56) References Cited

U.S. PATENT DOCUMENTS 3,503,783 A * 3/1970 Evans ...................... B01J 13/22
264/4.3
4,696,863 A 9/1987 Matsushita et al.
(Continued)

FOREIGN PATENT DOCUMENTS

CN 107249545 A 10/2017
EP 1780731 A1 5/2007
(Continued)

OTHER PUBLICATIONS

English Translation of WO 2010003762 A1. Obtained Oct. 18, 2016 at https://worldwide.espacenet.com/publicationDetails/biblio?CC=WO&NR=2010003762A1&KC=A1&FT=D&ND=3&date=20100114&DB=EPODOC&locale=en_EP#.*
(Continued)

*Primary Examiner* — Arrie L Reuther
(74) *Attorney, Agent, or Firm* — Schwegman Lundberg & Woessner, P.A.

(57) ABSTRACT

Accordingly, there are provided coated microcapsules including a microcapsule, said microcapsules including a polymeric shell and a liquid core material encapsulated therein; and a metallic coating surrounding said microcapsules; wherein the metallic coating includes particles of a first metal adsorbed on said polymeric shell and a film of a second metal formed thereon; and wherein the metallic
(Continued)

coating has a maximum thickness of 1000 nm; and methods and formulations related thereto.

15 Claims, 9 Drawing Sheets

(51) Int. Cl.
  C23C 18/30     (2006.01)
  A01N 25/28     (2006.01)
  B01J 13/22     (2006.01)
  C09B 67/02     (2006.01)
  C11D 3/50      (2006.01)
  C11D 3/02      (2006.01)
  C11D 17/00     (2006.01)
  A23L 27/00     (2016.01)

(52) U.S. Cl.
  CPC ........ *C09B 67/0097* (2013.01); *C11B 9/0007* (2013.01); *C11B 9/0019* (2013.01); *C11D 3/02* (2013.01); *C11D 3/505* (2013.01); *C11D 17/0039* (2013.01); *C23C 18/1641* (2013.01); *C23C 18/30* (2013.01)

(58) Field of Classification Search
  USPC ............................................................ 512/4
  See application file for complete search history.

(56) References Cited

U.S. PATENT DOCUMENTS

| | | | |
|---|---|---|---|
| 4,756,906 A | 7/1988 | Sweeny | |
| 4,795,260 A | 1/1989 | Schuur et al. | |
| 4,818,522 A | 4/1989 | Ferentchak et al. | |
| 8,679,629 B2 | 3/2014 | Zhao et al. | |
| 2002/0197404 A1 | 12/2002 | Lee et al. | |
| 2005/0158390 A1 | 7/2005 | Rana et al. | |
| 2007/0098976 A1 | 5/2007 | Lee et al. | |
| 2008/0081193 A1 | 4/2008 | Ou et al. | |
| 2009/0253612 A1 | 10/2009 | Mushock et al. | |
| 2010/0325812 A1 | 12/2010 | Panandiker et al. | |
| 2011/0008427 A1* | 1/2011 | Biggs .................. | A61K 8/11 424/463 |
| 2012/0237578 A1 | 9/2012 | Lei et al. | |
| 2013/0040817 A1* | 2/2013 | Dreher .................. | A01N 25/28 504/359 |
| 2013/0045877 A1 | 2/2013 | Yap et al. | |
| 2015/0258219 A1 | 9/2015 | Kataoka et al. | |
| 2016/0168509 A1 | 6/2016 | Hitchcock et al. | |
| 2016/0168510 A1 | 6/2016 | Tasker et al. | |
| 2016/0168511 A1 | 6/2016 | Hitchcock et al. | |

FOREIGN PATENT DOCUMENTS

| | | | |
|---|---|---|---|
| GB | 1359492 | 7/1974 | |
| GB | 2473870 | 3/2011 | |
| JP | 61225115 | 10/1986 | |
| KR | 2006096526 | 9/2006 | |
| KR | 100758786 | 9/2007 | |
| KR | 20080020857 A | 3/2008 | |
| WO | WO-2005057163 A2 | 6/2005 | |
| WO | WO-2009037482 A2 | 3/2009 | |
| WO | WO 2010/003762 A1 | 1/2010 | |
| WO | WO 2010003762 A1 * | 1/2010 | ............. B01J 13/22 |
| WO | WO-2014058079 A1 | 4/2014 | |
| WO | WO-2016/100477 A1 | 6/2016 | |
| WO | WO-2016/100482 A1 | 6/2016 | |
| WO | WO-2016/100492 A1 | 6/2016 | |
| WO | WO-2016/100499 A1 | 6/2016 | |
| WO | WO-2016100479 A1 | 6/2016 | |

OTHER PUBLICATIONS

PCT International Search Report dated Feb. 26, 2016—5 pages.
PCT International Search Report dated Apr. 25, 2016—4 pages.
PCT International Search Report dated Apr. 5, 2016—5 pages.
All Office Actions U.S. Appl. No. 14/971,608.
All Office Actions U.S. Appl. No. 14/971,754.
All Office Actions U.S. Appl. No. 14/971,783.
All Office Actions U.S. Appl. No. 14/971,805.
Olivier J. Cayre, Polymer Based Functional Particulates: Design, Synthesis and Applications, University of Loughborough, pp. 1-44, Nov. 2014.
Andrew Loxley, et al., "Preparation of Poly(methylmethacrylate) Microcapsules with Liquid Cores", Journal of Colloid and Interface Science, vol. 208, No. 1, pp. 49-62, Dec. 1, 1998.
Horiuchi, et al., "Platinum Colloid Catalyzed Etchingless Gold Electroless Plating with Strong Adhesion to Polymers", Surface and Coating Technology, vol. 204, pp. 3811-3817, 2010.
Tatsuo, et al., "Preparation of Polymer Core-Shell Particles Supporting Gold Nanoparticles", Colloids and Surfaces A: Physiocochemical and Engineering Aspects, vol. 377, pp. 63-69, 2011.
Conghui, et al., "Platinum-Nanoparticle Supported Core-Shell Polymer Nanospheres with Unexpected Water Stability and Facile Further Modification", Nanotechnology, vol. 23, 9 pages, Apr. 5, 2012.
Song, et al. "Thermal Stability of Composite Phase Change Material Microcapsules Incorporated with Silver Nano-Particles", Polymer, vol. 48, pp. 3317-3323, 2007.
Lin, et al., "Preparation of PMMA-Ni Core-Shell Composite Particles by Electroless Plating on Polyelectrolyte-Modified PMMA Beads", Applied Surface Science, vol. 282, pp. 741-745, 2013.
Kim, et al., "Synthesis and Electrical Resistivity of the Monodisperse PMMA/Ag Hybrid Particles", Materials Chemistry and Physics, vol. 134, pp. 814-820, 2012, Inha University, Republic of Korea.
Patchan, et al., "Liquid Filled Metal Microcapsules", ACS Appl. Mater. Interfaces, vol. 4, pp. 2406-2412, 2012, The John Hopkins University, USA.
U.S. Appl. No. 14/971,608, filed Dec. 16, 2015, Compositions Providing Delayed Release of Actives.
U.S. Appl. No. 14/971,754, filed Dec. 16, 2015, Coated Microcapsules.
U.S. Appl. No. 14/971,783, filed Dec. 16, 2015, Coated Microcapsules.
U.S. Appl. No. 14/971,805, filed Dec. 16, 2015, Coated Microcapsules.
"U.S. Appl. No. 14/971,754, Non Final Office Action dated Jan. 26, 2017", 22 pgs.
"U.S. Appl. No. 14/971,783, Non Final Office Action dated Feb. 1, 2017", 23 pgs.
"U.S. Appl. No. 14/971,805, Respnose filed Mar. 23, 2017 to Non Final Office Action dated Oct. 27, 2016", 10 pgs.
"U.S. Appl. No. 14/971,805, Response filed Aug. 23, 2016 to Restriction Requirement dated Jun. 28, 2016", 1 pgs.
"U.S. Appl. No. 14/971,805, Restriction Requirement dated Jun. 28, 2016", 6 pgs.
English Machine Translation of WO2010003762A1, published on Jan. 14, 2014, 37 pgs.
"International Application Serial No. PCT/US2015/066041, Written Opinion dated Feb. 26, 2016", 6 pgs.
"International Application Serial No. PCT/US2015/066048, Written Opinion dated Apr. 5, 2016", 5 pgs.
"International Application Serial No. PCT/US2015/066059, Written Opinion dated Apr. 5, 2016", 4 pgs.
"International Application Serial No. PCT/US2015/066067, Written Opinion dated Apr. 25, 2016", 5 pgs.
Qingwen, Song, et al., "Thermal stability of composite phase change material microcapsules incorporated with silver", *Polymer*, 48(11), (May 11, 2007), 3317-3323.
Tatsuo, Taniguchi, et al., "Preparation of polymer coreshell particles supporting gold nanoparticles", *Colloids and Surfaces A; Physicochemical and Engineering Aspects*, 377(1), (Dec. 10, 2010), 63-69.

(56) References Cited

OTHER PUBLICATIONS

Yuan, Conghui, et al., "Platinum-nanoparticle-supported core shell polymer nanospheres with unexpected water stability and facile further modification", *Nanotechnology*, 23(17), 175301, (2012), 9 pgs.

"International Application Serial No. PCT/US2015/066043, Written Opinion dated Apr. 25, 2016", 5 pgs.

"U.S. Appl. No. 14/971,608, Final Office Action dated Aug. 31, 2017", 11 pgs.

"U.S. Appl. No. 14/971,608, Response filed Jul. 31, 2017 tp Non Final Office Action dated Jan. 31, 2017", 11 pgs.

"U.S. Appl. No. 14/971,754, Final Office Action dated Aug. 31, 2017", 10 pgs.

"U.S. Appl. No. 14/971,754, Response filed Jul. 26, 2017 to Non Final Office Action dated Jan. 26, 2017", 9 pgs.

"U.S. Appl. No. 14/971,783, Final Office Action dated Aug. 31, 2017", 10 pgs.

"U.S. Appl. No. 14/971,783, Response filed Aug. 1, 2017 to Non Final Office Action dated Feb. 1, 2017", 8 pgs.

"U.S. Appl. No. 14/971,805, Final Office Action dated May 10, 2017", 12 pgs.

"European Application Serial No. 15823075.5, Office Action dated Aug. 1, 2007", 2 pgs.

* cited by examiner

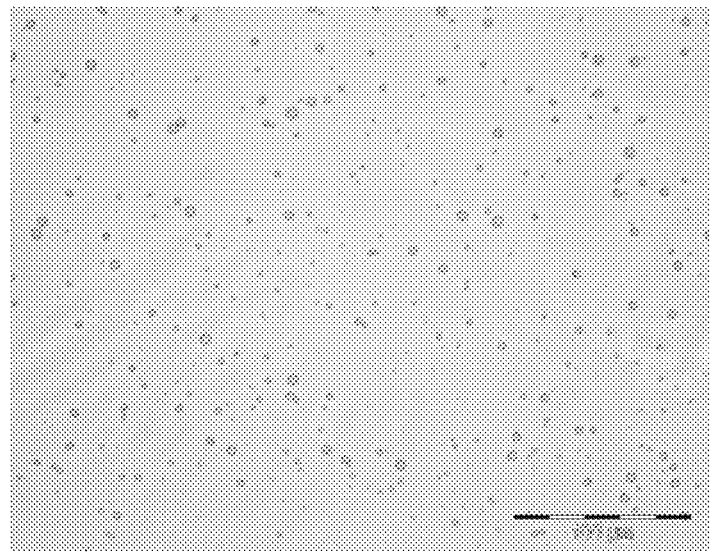
Fig. 3A
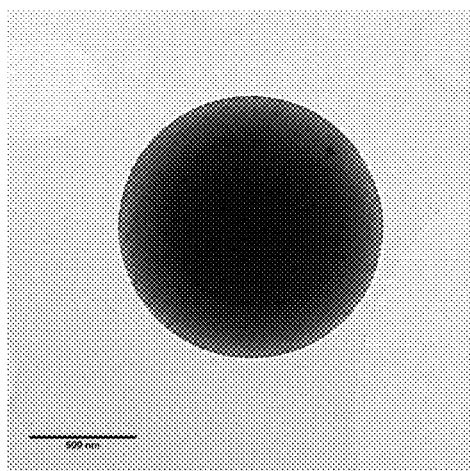 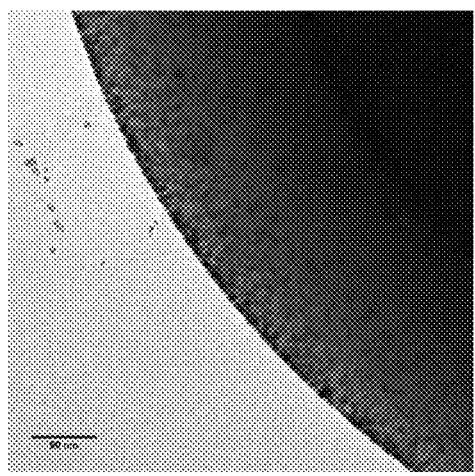
Fig. 3B　　　　　　　　　　　Fig. 3C

US 9,944,886 B2

COATED MICROCAPSULES

FIELD

The present disclosure relates to microcapsules comprising a liquid core material, to processes for their preparation and to formulations including the same. More particularly, the present disclosure relates to microcapsules including a liquid core material which can be released in a controlled manner during use. The microcapsules find application in fine fragrance formulations and other consumer products where controlled release of active ingredients is desired.

BACKGROUND

The encapsulation of liquid substances and their controlled, targeted delivery is important to industry. However, the efficient encapsulation of liquid substances, especially volatile substances, has proven difficult. Although applications of encapsulation techniques are increasing year on year, there remain significant shortcomings and limitations. In particular, the encapsulation of volatile compounds is an area in which little progress has been made.

Particular problems are encountered in the encapsulation of perfume oils, which are volatile substances found in fine fragrances and other fragrance formulations. Although the use of microcapsules to encapsulate perfume oils has been proposed, fragrance formulations typically contain polar solvents such as ethanol in which the microcapsules are dispersed. These polar solvents can readily penetrate the wall of the microcapsules, causing the perfume oils to leach prematurely from the microcapsules. It would be desirable to provide microcapsules which enable perfume oils to be released in a controlled manner during use, e.g. by rupturing the microcapsules during normal human movement.

There is a need in the art for improved microcapsules for encapsulating liquid substances, especially microcapsules which exhibit an improved release profile. In particular, there is a need for microcapsules for encapsulating liquid substances such as perfume oils, wherein the microcapsules are substantially impermeable to polar solvents such as ethanol yet, at the same time, are capable of releasing their contents in a controlled manner during use. There is also a need for improved processes for the preparation of microcapsules.

SUMMARY

Accordingly, there is provided a coated microcapsule comprising:
a microcapsule comprising a polymeric shell and a liquid core material encapsulated therein; and
a metallic coating surrounding said microcapsule;
wherein the metallic coating comprises particles of a first metal adsorbed on said polymeric shell and a film of a second metal formed thereon; and wherein the metallic coating has a maximum thickness of 1000 nm.

Accordingly, there is provided a process for preparing a coated microcapsule, the process comprising:
providing a microcapsule comprising a polymeric shell and a liquid core material encapsulated therein; and
coating said microcapsule with a metallic coating which surrounds said microcapsule, wherein the metallic coating has a maximum thickness of 1000 nm;
wherein the step of coating said microcapsule comprises:
adsorbing particles of a first metal on said polymeric shell; and
forming a film of a second metal on said particles of the first metal.

In other aspects, the disclosure provides a plurality of coated microcapsules, as well as formulations comprising the same. Also provided are methods of fragrancing a substrate using a coated microcapsule.

The coated microcapsules offer various advantages and benefits. In particular, volatile liquid substances such as perfume oils can be encapsulated in microcapsules which are substantially impermeable to polar solvents such as ethanol yet, at the same time, can be ruptured during use. Moreover, the preparation processes disclosed herein enable the coated microcapsules to be prepared in a facile manner. In particular, the processes described herein may enable a metallic coating to be applied in only a small number of steps.

BRIEF DESCRIPTION OF THE DRAWINGS

FIG. 1A is converted to an uncoated microcapsule FIG. 1B comprising a polymeric shell and a liquid core material. Particles of a first metal are adsorbed onto the microcapsule surface FIG. 1C and a continuous film of a second metal is then applied, yielding a coated microcapsule FIG. 1D. Shown beneath the schematic diagram are corresponding optical microscopy FIG. 1A, transmission electron microscopy (TEM) (FIG. 1B, FIG. 1C) and scanning electron microscopy (SEM) FIG. 1D images of a microcapsule formed by such a process.

FIG. 2A an SEM image of the uncoated microcapsules; FIG. 2B a TEM image showing the platinum nanoparticles adsorbed on the outer surface of the microcapsules; and FIG. 2C an SEM image showing the continuous gold film.

FIGS. 3A, 3B, 3C, 3D and 3E provide optical, SEM and TEM images obtained at various stages of preparation of a coated microcapsule, the microcapsule comprising a PEMA shell, a toluene core and a metallic coating comprising a continuous silver film formed on a layer of borohydride-stabilised gold nanoparticles. Shown are: FIG. 3A an optical image showing the uncoated microcapsules; FIG. 3B and FIG. 3C TEM images showing the borohydride-stabilised gold nanoparticles adsorbed on the surface of the microcapsules; and FIG. 3D an SEM image showing the continuous silver film. Also shown is: FIG. 3E an EDX graph indicating the silver content of the metallic film.

FIG. 6A an optical micrograph showing the uncoated microcapsules; FIG. 6B a TEM image showing the PVP-stabilised platinum nanoparticles adsorbed on the surface of the microcapsules; and FIG. 6C an SEM image showing the gold film on the microcapsules.

DESCRIPTION OF VARIOUS EMBODIMENTS

Liquid Core Material

Figures 1A, 1B, 1C, 1D:
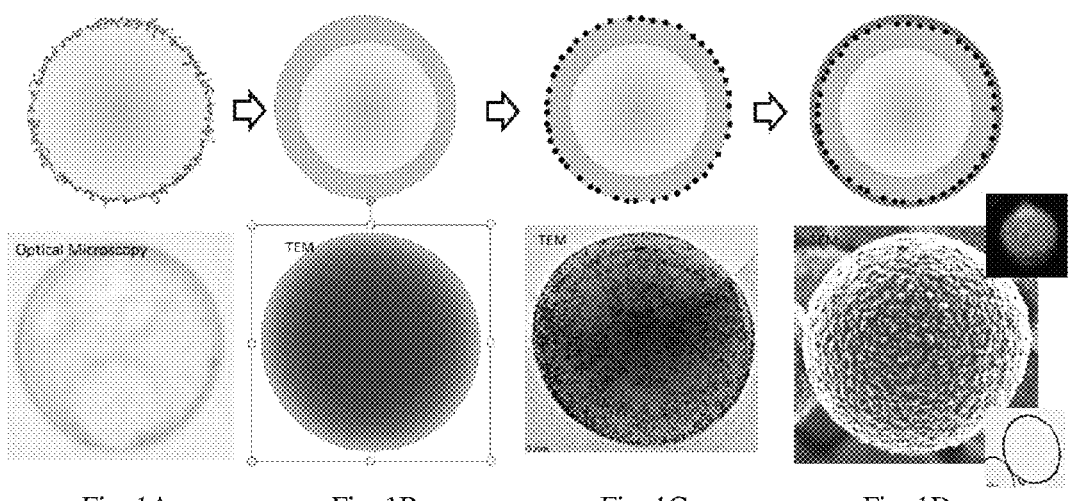
FIGS. 1A, 1B, 1C and 1D depict a schematic diagram illustrating a process for preparing an exemplary coated microcapsule wherein a schematic diagram is in the upper portion and beneath the schematic diagram is the corresponding microscopy. In the depicted process, emulsion template

The coated microcapsules may comprise a liquid core material encapsulated by a polymeric shell. The term "liquid core material" as used herein refers to a core material formed of one or more components, at least 90% by weight of which are liquid at standard ambient temperature and pressure. The term "standard ambient temperature and pressure" (or "STP") refers to a temperature of 25° C. and an absolute pressure of 100 kPa. Preferably, the liquid core material comprises at least 95% by weight, e.g. at least 98% by weight, of one or more components which are liquid at standard ambient temperature and pressure. In some examples, the liquid core material consists of one or more components which are liquid at standard ambient temperature and pressure. In some examples, the liquid core material includes a mixture of liquids and a solid, non-limiting examples of which include a mixture of vanillin and perfume oils.

The liquid core material may be present in the coated microcapsule in an amount of at least 1% by weight of the microcapsule, preferably in an amount of at least 30% by weight, and more preferably in an amount of at least 60% by weight. In some examples, the liquid core material is present in the coated microcapsule in an amount of from 10 to 99.9% by weight of the coated microcapsule, alternatively from 40 to 90% by weight of the coated microcapsule, alternatively from 50 to 90% by weight, alternatively from 60 to 80% by weight.

In some examples, the liquid core material comprises one or more components which are volatile. Unless otherwise specified, the term "volatile" as used herein refers to those materials that are liquid or solid under ambient conditions and which have a measurable vapour pressure at 25° C. These materials typically have a vapour pressure of greater than about 0.0000001 mm Hg, e.g. from about 0.02 mm Hg to about 20 mm Hg, and an average boiling point typically less than about 250° C., e.g. less than about 235° C.

The liquid core material may consist of a single material or it may be formed of a mixture of different materials. In some examples, the liquid core material comprises one or more active ingredients. The coated microcapsules described herein are useful with a wide variety of active ingredients (i.e. "core materials") including, by way of illustration and without limitation, perfumes; brighteners; insect repellants; silicones; waxes; flavors; vitamins; fabric softening agents; depilatories; skin care agents; enzymes; probiotics; dye polymer conjugate; dye clay conjugate; perfume delivery system; sensates in one aspect a cooling agent; attractants, in one aspect a pheromone; anti-bacterial agents; dyes; pigments; bleaches; flavorants; sweeteners; waxes; pharmaceuticals; fertilizers; herbicides and mixtures thereof. The microcapsule core materials can include materials which alter rheology or flow characteristics, or extend shelf life or product stability. Essential oils as core materials can include, for example, by way of illustration wintergreen oil, cinnamon oil, clove oil, lemon oil, lime oil, orange oil, peppermint oil and the like. Dyes can include fluorans, lactones, indolyl red, I6B, leuco dyes, all by way of illustration and not limitation. Particularly useful encapsulated materials are volatile fragrances.

The liquid core material preferably comprises one or more components which are oil-soluble. The use of a liquid core material which is oil-soluble will be preferable having regard to, inter alia, the production of the microcapsules, which will typically be prepared by a process which involves the use of an oil-in-water emulsion in which the liquid core material is present in the non-aqueous (oil) phase. In some examples, the liquid core material is substantially free of water. In particular, the amount of water present in the liquid core material may be less than 5% by weight, e.g. less than 1% by weight, of the liquid core material. More preferably, the liquid core material consists of one or more oil-soluble components.

The liquid core material is preferably free of compounds which are capable of reacting with any of the compounds that are used to form the polymeric shell of the microcapsules. In particular, the liquid core material is preferably free of any polymerisable compounds.

In some examples, the liquid core material comprises a perfume oil formed of one or more perfume raw materials. The term "perfume oil" as used herein refers to the perfume raw material, or mixture of perfume raw materials, that is used to impart an overall pleasant odour profile to the liquid core material. Thus, where different perfume raw materials are present in the liquid core material, this term refers to the overall mixture of perfume raw materials in the liquid core material. The choice of the perfume raw materials defines both the odour intensity and character of the liquid core material. The perfume oils utilised in the coated microcapsules may be relatively simple in their chemical make-up, for example consisting of only a single perfume raw material, or they may comprise complex mixtures of perfume raw materials, all chosen to provide a desired odour.

The perfume oil may comprise one or more perfume raw materials having a boiling point of less than 500° C., e.g. less than 400° C., e.g. less than 350° C. The boiling points of many perfume raw materials are given in, e.g., "Perfume and Flavor Chemicals (Aroma Chemicals)" by Steffen Arctander (1969) and other textbooks known in the art.

The one or more perfume raw materials will typically be hydrophobic. The hydrophobicity of a given compound may be defined in terms of its partition coefficient. The term "partition coefficient" as used herein refers to the ratio between the equilibrium concentration of that substance in n-octanol and in water, and is a measure of the differential solubility of said substance between these two solvents. Partition coefficients are described in more detail in U.S. Pat. No. 5,578,563.

The term "log P" refers to the logarithm to the base 10 of the partition coefficient. Values of log P values can be readily calculated using a program called "CLOGP" which is available from Daylight Chemical Information Systems Inc., 30 Irvine Calif., U.S.A. or using Advanced Chemistry Development (ACD/Labs) Software 13375P 9 V11.02 (© 1994-2014 ACD/Labs). In some examples, the perfume oil comprises one or more perfume raw materials having a calculated log P (C log P) value of about −0.5 or greater, e.g. greater than 0.1, e.g. greater than 0.5, greater than 1.0. In some examples, the perfume oil consists of one or more perfume raw materials having a C log P value of greater than 0.1, e.g. greater than 0.5, e.g. greater than 1.0.

In some examples, the perfume oil comprises one or more perfume raw materials selected from aldehydes, esters, alcohols, ketones, ethers, alkenes, nitriles, Schiff bases, and mixtures thereof.

Examples of aldehyde perfume raw materials include, without limitation, alpha-amylcinnamaldehyde, anisic aldehyde, decyl aldehyde, lauric aldehyde, methyl n-nonyl acetaldehyde, methyl octyl acetaldehyde, nonylaldehyde, benzenecarboxaldehyde, neral, geranial, 1,1-diethoxy-3,7-dimethylocta-2,6-diene, 4-isopropylbenzaldehyde, 2,4-dimethyl-3-cyclohexene-1-carboxaldehyde, alpha-methyl-p-isopropyldihydrocinnamaldehyde, 3-(3-isopropylphenyl) butanal, alpha-hexylcinnamaldehyde, 7-hydroxy-3,7-dimethyloctan-1-al, 2,4-dimethyl-3-cyclohexene-1-carboxaldehyde, octyl aldehyde, phenylacetaldehyde, 2,4-dimethyl-3-cyclohexene-1-carboxaldehyde, hexanal, 3,7-dimethyloctanal, 6,6-dimethylbicyclo[3.1.1]hept-2-ene-2-butanal, nonanal, octanal, 2-nonenal undecenal, 2-methyl-4-(2,6,6-trimethyl-1-cyclohexenyl-1)-2-butenal, 2,6-dimethyloctanal, 3-(p-isopropylphenyl)propionaldehyde, 3-phenyl-4-pentenal citronellal, o/p-ethyl-alpha, alpha, 9-decenal, dimethyldihydrocinnamaldehyde, p-isobutyl-alphamethylydrocinnamaldehyde, cis-4-decen-1-al, 2,5-dimethyl-2-ethenyl-4-hexenal, trans-2-methyl-2-butenal, 3-methylnonanal, alpha-sinensal, 3-phenylbutanal, 2,2-dimethyl-3-phenylpropionaldehyde, m-tertbutyl-alpha-methyl-dihydrocinnamic aldehyde, geranyl oxyacetaldehyde, trans-4-decen-1-al, methoxycitronellal, and mixtures thereof.

Examples of ester perfume raw materials include, without limitation, allyl cyclohexane-propionate, allyl heptanoate, allyl amyl glycolate, allyl caproate, amyl acetate (n-pentyl acetate), amyl propionate, benzyl acetate, benzyl propionate, benzyl salicylate, cis-3-hexenylacetate, citronellyl acetate, citronellyl propionate, cyclohexyl salicylate, dihydro isojasmonate, dimethyl benzyl carbinyl acetate, ethyl acetate, ethyl acetoacetate, ethyl butyrate, ethyl-2-methyl butyrate, ethyl-2-methyl pentanoate, fenchyl acetate (1,3,3-trimethyl-2-norbornanyl acetate), tricyclodecenyl acetate, tricyclodecenyl propionate, geranyl acetate, cis-3-hexenyl isobutyrate, hexyl acetate, cis-3-hexenyl salicylate, n-hexyl salicylate, isobornyl acetate, linalyl acetate, p-t-butyl cyclohexyl acetate, (−)-L-menthyl acetate, o-t-butylcyclohexyl acetate, methyl benzoate, methyl dihydro isojasmonate, alpha-methylbenzyl acetate, methyl salicylate, 2-phenylethyl acetate, prenyl acetate, cedryl acetate, cyclabute, phenethyl phenylacetate, terpinyl formate, citronellyl anthranilate, ethyl tricyclo[5.2.1.0-2,6]decane-2-carboxylate, n-hexyl ethyl acetoacetate, 2-tertbutyl-4-methyl cyclohexyl acetate, formic acid, 3,5,5-trimethylhexyl ester, phenethyl crotonate, cyclogeranyl acetate, geranyl crotonate, ethyl geranate, geranyl isobutyrate, 3,7-dimethyl-ethyl 2-nonynoate-2,6-octadienoic acid methyl ester, citronellyl valerate, 2-hexenyl-cyclopentanone, cyclohexyl anthranilate, L-citronellyl tiglate, butyl tiglate, pentyl tiglate, geranyl caprylate, 9-decenyl acetate, 2-isopropyl-5-methylhexyl-1 butyrate, n-pentyl benzoate, 2-methylbutyl benzoate (and mixtures thereof with pentyl benzoate), dimethyl benzyl carbinyl propionate, dimethyl benzyl carbinyl acetate, trans-2-hexenyl salicylate, dimethyl benzyl carbinyl isobutyrate, 3,7-dimethyloctyl formate, rhodinyl formate, rhodinyl isovalerate, rhodinyl acetate, rhodinyl butyrate, rhodinyl propionate, cyclohexylethyl acetate, neryl butyrate, tetrahydrogeranyl butyrate, myrcenyl acetate, 2,5-dimethyl-2-ethenylhex-4-enoic acid, methyl ester, 2,4-dimethylcyclohexane-1-methyl acetate, ocimenyl acetate, linalyl isobutyrate, 6-methyl-5-heptenyl-1 acetate, 4-methyl-2-pentyl acetate, n-pentyl 2-methylbutyrate, propyl acetate, isopropenyl acetate, isopropyl acetate, 1-methylcyclohex-3-ene-carboxylic acid, methyl ester, propyl tiglate, propyl/isobutyl cyclopent-3-enyl-1-acetate (alphavinyl), butyl 2-furoate, ethyl 2-pentenoate, (E)-methyl 3-pentenoate, 3-methoxy-3-methylbutyl acetate, n-pentyl crotonate, n-pentyl isobutyrate, propyl formate, furfuryl butyrate, methyl angelate, methyl pivalate, prenyl caproate, furfuryl propionate, diethyl malate, isopropyl 2-methylbutyrate, dimethyl malonate, bornyl formate, styralyl acetate, 1-(2-furyl)-1-propanone, 1-citronellyl acetate, 3,7-dimethyl-1,6-nonadien-3-yl acetate, neryl crotonate, dihydromyrcenyl acetate, tetrahydromyrcenyl acetate, lavandulyl acetate, 4-cyclooctenyl isobutyrate, cyclopentyl isobutyrate, 3-methyl-3-butenyl acetate, allyl acetate, geranyl formate, cis-3-hexenyl caproate, and mixtures thereof.

Examples of alcohol perfume raw materials include, without limitation, benzyl alcohol, beta-gamma-hexenol (2-hexen-1-ol), cedrol, citronellol, cinnamic alcohol, p-cresol, cumic alcohol, dihydromyrcenol, 3,7-dimethyl-1-octanol, dimethyl benzyl carbinol, eucalyptol, eugenol, fenchyl alcohol, geraniol, hydratopic alcohol, isononyl alcohol (3,5,5-trimethyl-1-hexanol), linalool, methyl chavicol (estragole), methyl eugenol (eugenyl methyl ether), nerol, 2-octanol, patchouli alcohol, phenyl hexanol (3-methyl-5-phenyl-1-pentanol), phenethyl alcohol, alpha-terpineol, tetrahydrolinalool, tetrahydromyrcenol, 4-methyl-3-decen-5-ol, 1-3,7-dimethyloctane-1-ol, 2-(furfuryl-2)-heptanol, 6,8-dimethyl-2-nonanol, ethyl norbornyl cyclohexanol, beta-methyl cyclohexane ethanol, 3,7-dimethyl-(2), 6-octen (adien)-1-ol, trans-2-undecen-1-ol, 2-ethyl-2-prenyl-3-hexenol, isobutyl benzyl carbinol, dimethyl benzyl carbinol, ocimenol, 3,7-dimethyl-1,6-nonadien-3-ol (cis & trans), tetrahydromyrcenol, alpha-terpineol, 9-decenol-1, 2-(2-hexenyl)-cyclopentanol, 2,6-dimethyl-2-heptanol, 3-methyl-1-octen-3-ol, 2,6-dimethyl-5-hepten-2-ol, 3,7,9-trimethyl-1,6-decadien-3-ol, 3,7-dimethyl-6-nonen-1-ol, 3,7-dimethyl-1-octyn-3-ol, 2,6-dimethyl-1,5,7-octatrienol-3, dihydromyrcenol, 2,6,-trimethyl-5,9-undecadienol, 2,5-dimethyl-2-propylhex-4-enol-1, (Z)-3-hexenol, o,m,p-methylphenylethanol, 2-methyl-5-phenyl-1-pentanol, 3-methylphenethyl alcohol, para-methyl dimethyl benzyl carbinol, methyl benzyl carbinol, p-methylphenylethanol, 3,7-dimethyl-2-octen-1-ol, 2-methyl-6-methylene-7-octen-4-ol, and mixtures thereof.

Examples of ketone perfume raw materials include, without limitation, oxacycloheptadec-10-en-2-one, benzylacetone, benzophenone, L-carvone, cis-jasmone, 4-(2,6,6-trimethyl-3-cyclohexen-1-yl)-but-3-en-4-one, ethyl amyl ketone, alpha-ionone, ionone beta, ethanone, octahydro-2,3,8,8-tetramethyl-2-acetonaphthalene, alpha-irone, 1-(5,5-dimethyl-1-cyclo-hexen-1-yl)-4-penten-1-one, 3-nonanone, ethyl hexyl ketone, menthone, 4-methyl-acetophenone, gamma-methyl ionone, methyl pentyl ketone, methyl heptenone (6-methyl-5-hepten-2-one), methyl heptyl ketone, methyl hexyl ketone, delta muscenone, 2-octanone, 2-pentyl-3-methyl-2-cyclopenten-1-one, 2-heptylcyclopentanone, alpha-methylionone, 3-methyl-2-(trans-2-pentenyl)-cyclopentenone, octenyl cyclopentanone, n-amylcyclopentenone, 6-hydroxy-3,7-dimethyloctanoic acid lactone, 2-hydroxy-2-cyclohexen-1-one, 3-methyl-4-phenyl-3-buten-2-one, 2-pentyl-2,5,5-trimethylcyclopentanone, 2-cyclopentylcyclopentanol-1, 5-methylhexan-2-one, gamma-dodecalactone, delta-dodecalactone delta-dodecalactone, gamma-nonalactone, delta-nonalactone, gamma-octalactone, delta-undecalactone, gamma-undecalactone, and mixtures thereof.

Examples of ether perfume raw materials include, without limitation, p-cresyl methyl ether, 4,6,6,7,8, 8-hexamethyl-1,3,4,6,7,8-hexahydro-cyclopenta(G)-2-benzopyran, beta-naphthyl methyl ether, methyl isobutenyl tetrahydropyran, 5-acetyl-1,1,2,3,3,6-hexamethylindan (phantolide), 7-acetyl-1,1,3,4,4,6-hexamethyltetralin (tonalid), 2-phenylethyl-3-methylbut-2-enyl ether, ethyl geranyl ether, phenylethyl isopropyl ether, and mixtures thereof.

Examples of alkene perfume raw materials include, without limitation, allo-ocimene, camphene, beta-caryophyllene, cadinene, diphenylmethane, d-limonene, lymolene, beta-myrcene, para-cymene, 2-alpha-pinene, beta-pinene, alpha-terpinene, gamma-terpinene, terpineolene, 7-methyl-3-methylene-1,6-octadiene, and mixtures thereof.

Examples of nitrile perfume raw materials include, without limitation, 3,7-dimethyl-6-octenenitrile, 3,7-dimethyl-2 (3), 6-nonadienenitrile, (2E,6Z)-2,6-nonadienenitrile, n-dodecane nitrile, and mixtures thereof.

Examples of Schiff base perfume raw materials include, without limitation, citronellyl nitrile, nonanal/methyl anthranilate, N-octylidene-anthranilic acid methyl ester, hydroxycitronellal/methyl anthranilate, cyclamen aldehyde/methyl anthranilate, methoxyphenylpropanal/methyl anthranilate, ethyl p-aminobenzoate/hydroxycitronellal, citral/methyl anthranilate, 2,4-dimethylcyclohex-3-enecarbaldehyde methyl anthranilate, hydroxycitronellal-indole, and mixtures thereof.

Non-limiting examples of other the perfume raw materials useful herein include pro-fragrances such as acetal pro-fragrances, ketal pro-fragrances, ester pro-fragrances, hydrolyzable inorganic-organic pro-fragrances, and mixtures thereof. The fragrance materials may be released from the pro-fragrances in a number of ways. For example, the fragrance may be released as a result of simple hydrolysis, or by a shift in an equilibrium reaction, or by a pH-change, or by enzymatic release.

In some examples, the perfume oil comprises one or more of the perfume raw materials recited in the above lists. In some examples, the perfume oil comprises a plurality of perfume raw materials recited in the above lists.

In some examples, the liquid core material comprises one or more perfume oils of natural origin. In some examples, the liquid core material comprises one or more perfume oils selected from musk oil, civet, castoreum, ambergris, nutmeg extract, cardamon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomile oil, clove oil, sage oil, neroli oil, labdanum oil, eucalyptus oil, verbena oil, mimosa extract, narcissus extract, carrot seed extract, jasmine extract, olibanum extract, rose extract, and mixtures thereof. One or more of these perfume oils may be used with one or more of the perfume raw materials recited above.

The perfume oil may be present in the liquid core material in an amount of from 0.1 to 100% by weight of the liquid core material. In some examples, the liquid core material consists essentially, e.g. consists of, a perfume oil. In some examples, the perfume oil is present in the liquid core material in an amount of at least 10% by weight of the liquid core material, preferably at least 20% by weight, and more preferably at least 30% by weight. In some examples, the perfume oil is present in the liquid core material in an amount of from 80-100% by weight of the liquid core material, alternatively less than 80% by weight of the liquid core material, alternatively less than 70% by weight, alternatively less than 60% by weight. In some examples, the perfume oil is present in an amount of from 10 to 50% by weight of the liquid core material, more preferably from 15 to 30%. Preferred liquid core materials contain from 10 to 80% by weight of a perfume oil, preferably from 20 to 70%, more preferably from 30 to 60%.

The liquid core material may comprise one or more components in addition to the perfume oil. For example, the liquid core material may comprise one or more diluents. Examples of diluents include mono-, di- and tri-esters of $C_4$-$C_{24}$ fatty acids and glycerine, isopropyl myristate, soybean oil, hexadecanoic acid, methyl ester, isododecane, and mixtures thereof. Where present, diluents are preferably present in the liquid core material in an amount of at least 1% by weight of the liquid core material, e.g. from 10 to 60% by weight of the liquid core material.

Polymeric Shell

The liquid core material is encapsulated by a polymeric shell. The coated microcapsules may be prepared by first forming the polymeric shell around the liquid core material to as to form an uncoated microcapsule, and subsequently forming the metallic coating. The term "uncoated microcapsule" as used herein refers to the microcapsule comprising the liquid core material prior to coating with the metallic coating.

The polymeric shell may comprise one or more polymeric materials. For example, the polymeric shell may comprise one or more polymers chosen from synthetic polymers, naturally-occurring polymers, and combinations thereof. Examples of synthetic polymers include, without limitation, nylon, polyethylenes, polyamides, polystyrenes, polyisoprenes, polycarbonates, polyesters, polyureas, polyurethanes, polyolefins, polysaccharides, epoxy resins, vinyl polymers, polyacrylates, and combinations thereof. Examples of synthetic polymers include, without limitation, silk, wool, gelatin, cellulose, alginate, proteins, and combinations thereof. The polymeric shell may comprise a homopolymer or a copolymer (e.g. a block copolymer or a graft copolymer).

In some examples, the polymeric shell comprises a polyacrylate, e.g. poly(methyl methacrylate) (PMMA) or poly (ethyl methacrylate) (PEMA). The polyacrylate may be present in an amount of at least 5%, at least 10%, at least 25%, at least 30%, at least 50%, at least 70%, or at least 90% of the weight of the polymeric shell.

In some examples, the polymeric shell comprises a polyacrylate random copolymer. For example, the polyacrylate random copolymer can comprise: an amine content of from 0.2 to 2.0% by weight of the total polyacrylate mass; a carboxylic acid content of from 0.6 to 6.0% by weight of the total polyacrylate mass; and a combination of an amine content of from 0.1 to 1.0% and a carboxylic acid content of from 0.3 to 3.0% by weight of the total polyacrylate mass.

In some examples, the microcapsule shell comprises a reaction product of a first mixture in the presence of a second mixture comprising an emulsifier, the first mixture comprising a reaction product of i) an oil soluble or dispersible amine with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator. In some examples, said amine is selected from the group consisting of aminoalkyl acrylates, alkyl aminoalkyl acrylates, dialkyl aminoalkyl acrylates, aminoalkyl methacrylates, alkylamino aminoalkyl methacrylates, dialkyl aminoalkyl methacrylates, tertiarybutyl aminoethyl methacrylates, diethylaminoethyl methacrylates, dimethylaminoethyl methacrylates, dipropylaminoethyl methacrylates, and mixtures thereof. In some examples, said amine is an aminoalkyl acrylate or aminoalkyl methacrylate.

In some examples, the polymeric shell comprises a reaction product of an amine with an aldehyde. For example, the polymeric shell may comprise a reaction product selected from urea cross-linked with formaldehyde or glutaraldehyde; melamine cross-linked with formaldehyde; gelatin-polyphosphate coacervates optionally cross-linked with gluteraldehyde; gelatin-gum arabic coacervates; cross-linked silicone fluids; polyamines reacted with polyisocyanates; acrylate monomers polymerized via free radical polymerization, and mixtures thereof. In some examples, the polymeric shell comprises a reaction product selected from urea-formaldehyde (i.e. the reaction product of urea cross-linked with formaldehyde) and melamine resin (i.e. melamine cross-linked with formaldehyde).

In some examples, the polymeric shell comprises gelatin, optionally in combination with one or more additional polymers. In some examples, the polymeric shell comprises gelatin and polyurea.

The polymeric shell may comprise one or more components in addition to the one or more wall-forming polymers. Preferably, the polymeric shell further comprises an emulsifier. In this regard, and as described in more detail below, encapsulation of the liquid core material may be achieved by providing an oil-in-water emulsion in which droplets of an oil (non-aqueous) phase comprising the liquid core material are dispersed in a continuous aqueous phase, and then forming a polymeric shell around the droplets. Such processes are typically performed in the presence of an emulsifier (also known as a stabiliser), which stabilises the emulsion and reduce the likelihood of aggregation of microcapsules during formation of the polymeric shell. Emulsifiers normally stabilise the emulsion by orienting themselves at the oil phase/aqueous phase interface, thus establishing a steric and/or charged boundary layer around each droplet. This layer serves as a barrier to other particles or droplets preventing their intimate contact and coalescence, thereby maintaining a uniform droplet size. Since the emulsifier will typically be retained in the polymeric shell, the polymeric shell of the microcapsules may comprise an emulsifier as an additional component. The emulsifier may be adsorbed on and/or absorbed in the polymeric shell of the microcapsules.

The emulsifier may be a polymer or a surfactant. The emulsifier may be a non-ionic, cationic, anionic, zwitterionic or amphoteric emulsifier. Examples of suitable emulsifiers include, without limitation, cetyl trimethylammonium bromide (CTAB), poly(vinyl alcohol) (PVA), poly(vinyl pyrrolidone) (PVP), poly(acrylic acid) (PAA), poly(methacrylic acid) (PMA), dodecyldimethyl ammonium bromide (DDAB), sodium dodecyl sulfate (SDS) and poly(ethylene glycol). In some examples, the emulsifier is selected from cetyl trimethylammonium bromide, poly(vinyl alcohol) and poly(vinyl pyrrolidone).

The uncoated microcapsules may be formed by emulsifying the liquid core material into droplets and forming a polymeric shell around the droplets. Microencapsulation of the liquid core material can be conducted using a variety of methods known in the art, including coacervation methods, in situ polymerisation methods and interfacial polymerisation methods. Such techniques are known in the art (see, e.g., "Microencapsulation: Methods and Industrial Applications", Edited by Benita and Simon, Marcel Dekker, Inc., 1996; U.S. Pat. No. 2,730,456; U.S. Pat. No. 2,800,457; U.S. Pat. No. 2,800,458; U.S. Pat. No. 4,552,811; U.S. Pat. No. 6,592,990; and U.S. 2006/0263518).

In some examples, the microcapsules are prepared a coacervation method which involves oil-in-water emulsification followed by solvent extraction. Such procedures are known in the art (see, e.g., Loxley et al., Journal of Colloid and Interface Science, vol. 208, pp. 49-62, 1998) and involve the use of a non-aqueous phase comprising a polymeric material that is capable of forming a polymeric shell, a poor solvent for the polymeric material, and a co-solvent which is a good solvent for the polymeric material. The non-aqueous and aqueous phases are emulsified, forming an oil-in-water emulsion comprising droplets of the non-aqueous phase dispersed in the continuous aqueous phase. The co-solvent is then partially or wholly extracted from the non-aqueous phase, causing the polymeric material to precipitate around the poor solvent, thereby encapsulating the poor solvent.

The uncoated microcapsules may be prepared by: (i) providing a non-aqueous phase comprising a polymeric material that is capable of forming a polymeric shell, a liquid core material which is a poor solvent for the polymeric material, and a co-solvent which is a good solvent for the polymeric material; (ii) providing an aqueous phase; (iii) emulsifying the non-aqueous phase and the aqueous phase to form an emulsion comprising droplets of the non-aqueous phase dispersed within the aqueous phase; and (iv) extracting at least a portion of the co-solvent from the non-aqueous phase such that the polymeric material precipitates around droplets comprising the liquid core material, thereby encapsulating the liquid core material.

In some examples, the polymeric material comprises a polyacrylate, e.g. poly(methyl methacrylate) (PMMA), poly(ethyl methacrylate) (PEMA) or a combination thereof. In some examples, the polymeric material consists of poly(methyl methacrylate) (PMMA) or poly(ethyl methacrylate) (PEMA).

Preferably, the polymeric material has a weight average molecular weight of at least 10 kDa, more preferably at least 50 kDa, more preferably at least 100 kDa. Preferably, the polymeric material has a weight average molecular weight of from 10 to 1000 kDa, more preferably from 50 to 800 kDa, more preferably from 100 to 600 kDa.

With regard to the chemical composition of the non-aqueous phase, the liquid core material is preferably present in an amount of from 0.5 to 50%, preferably from 1 to 45%, and more preferably from 3 to 40% by weight of the non-aqueous phase. The polymeric material is preferably present in the non-aqueous phase in an amount of from 0.5 to 15%, preferably from 1 to 10%, and more preferably from 2 to 8% by weight of the non-aqueous phase. The co-solvent is preferably present in an amount of from 40 to 98%, preferably from 50 to 98%, and more preferably from 60 to 95% by weight of the non-aqueous phase. In some examples, the non-aqueous phase consists of the liquid core material, the polymeric material and the co-solvent.

In some examples, the co-solvent is a volatile material, e.g. dichloromethane (DCM), and is extracted from the non-aqueous phase by evaporation. In this case, precipitation of the polymeric material may be aided by heating the emulsion to promote evaporation of the co-solvent. For instance, the method may be carried out at a temperature of at least 30° C.

Preferably, at least one of the aqueous and non-aqueous phases comprises an emulsifier. More preferably, the aqueous phase comprises an emulsifier. Examples of emulsifiers include, without limitation, poly(vinyl alcohol) (PVA), poly(vinyl pyrrolidone) (PVP), cetyl trimethylammonium bromide (CTAB) and mixtures thereof. In some examples, the emulsifier is present in an amount of from 0.01 to 50% by weight of the aqueous phase, preferably from 0.5 to 30%, and more preferably from 0.1 to 10% by weight.

In some examples, the polymeric shell is formed by an interfacial polymerisation process. For example, the polymeric shell may be prepared by an interfacial polymerisation process which involves the use of a non-aqueous phase comprising the liquid core material and one or more oil-soluble monomers; and an aqueous phase comprising one or more water-soluble monomers and an emulsifier. The non-aqueous and aqueous phases are emulsified to form an emulsion comprising droplets of the non-aqueous phase dispersed within the aqueous phase. The monomers are then polymerised, typically by heating, with polymerisation occurring at the interface between the non-aqueous phase and the aqueous phase.

Alternatively, the polymeric shell may be obtainable by interfacial polymerisation of a pre-polymer. Such processes may be used to prepare a range of different polymeric shell materials. For example, a polymeric shell comprising a polyacrylate, polyamine or polyurea material may be prepared by such a process.

Preferably, the polymeric material comprises a polyacrylate. In some examples, the polymeric shell comprises a polyacrylate and is obtainable by interfacial polymerisation of a pre-polymer, wherein the pre-polymer is obtained by reacting a mixture comprising: (i) an aminoalkyl acrylate monomer, an aminoalkyl methacrylate monomer, or a mixture thereof; and (ii) an acrylate monomer, a methacrylate monomer, an acrylate oligomer, a methacrylate oligomer, or a mixture thereof.

More preferably, the polymeric shell is prepared by a process comprising:

(i) providing a non-aqueous phase comprising the liquid core material, an amine monomer, a multifunctional acrylate or methacrylate monomer or oligomer, an acid and a free radical initiator;

(ii) reacting the amine monomer with the multifunctional acrylate or methacrylate monomer or oligomer to form a pre-polymer;

(iii) providing an aqueous phase comprising an emulsifier, an alkali or alkali salt, and optionally a free radical initiator;

(iv) contacting the non-aqueous phase with the aqueous phase under conditions such that an emulsion is formed comprising droplets of the non-aqueous phase dispersed in the aqueous phase; and (v) polymerising the pre-polymer to form a polymeric shell which encapsulates the liquid droplets.

The amine monomer is an oil-soluble or oil-dispersible amine monomer, more preferably an aminoalkyl acrylate or aminoalkyl methacrylate. In some examples, the amine monomer is selected from aminoalkyl acrylates, alkyl aminoalkyl acrylates, dialkyl aminoalkyl acrylates, aminoalkyl methacrylates, alkylamino aminoalkyl methacrylates, dialkyl aminoalkyl methacrylates, tertiarybutyl aminoethyl methacrylates, diethylaminoethyl methacrylates, dimethylaminoethyl methacrylates, dipropylaminoethyl methacrylates, and mixtures thereof. Preferred amine monomers are diethylaminoethyl methacrylate, dimethylaminoethyl methacrylate, tert-butyl aminoethyl methacrylate, and mixtures thereof. More preferably, the amine is tert-butylaminoethyl methacrylate and the multifunctional acrylate or methacrylate monomer or oligomer is a hexafunctional aromatic urethane acrylate oligomer.

In the above process, an aqueous phase comprising an emulsifer and an alkali or alkali salt is used. Examples of emulsifiers include, without limitation, poly(vinyl alcohol) (PVA), poly(vinyl pyrrolidone) (PVP), cetyl trimethylammonium bromide (CTAB), and mixtures thereof. In some examples, the alkali or alkali salt is sodium hydroxide.

The interfacial polymerisation process is preferably performed in the presence of a free radical initiator. Examples of suitable free radical initiators include azo initiators, peroxide, alkyl peroxides, dialkyl peroxides, peroxyesters, peroxycarbonates, peroxyketones and peroxydicarbonates. In some examples, the free radical initiator is selected from 2,2'-azobis-(2,4-dimethylpentanenitrile), 2,2'-azobis-(2-methyl-butyronitrile), and mixtures thereof. A free radical initiator may be present in the aqueous phase, the non-aqueous phase, or both.

In some examples, the microcapsules are prepared by an in situ polymerisation process. Such processes are known in the art and generally involve preparing an emulsion comprising droplets of the liquid core material dispersed in a continuous phase comprising a precursor material which can be polymerised to form a polymeric shell; and polymerising the precursor material to form a polymeric shell, thereby encapsulating the liquid droplets. The polymerisation process is similar to that of interfacial polymerisation processes, except in that no precursor materials for the polymeric shell are included in the liquid core material in in situ polymerisation processes. Thus, polymerisation occurs solely in the continuous phase, rather than on either side of the interface between the continuous phase and the core material.

Examples of precursor materials for the polymeric shell include, without limitation, pre-polymer resins such as urea resins, melamine resins, acrylate esters, and isocyanate resins. Preferably, the polymeric shell is formed by the polymerisation of a precursor material selected from: melamine-formaldehyde resins; urea-formaldehyde resins; monomeric or low molecular weight polymers of methylol melamine; monomeric or low molecular weight polymers of dimethylol urea or methylated dimethylol urea; and partially methylated methylol melamine.

The use of melamine-formaldehyde resins or urea-formaldehyde resins as the precursor material is particularly preferred. Procedures for preparing microcapsules comprising from such precursor materials are known in the art (see, e.g., U.S. Pat. No. 3,516,941, U.S. Pat. No. 5,066,419 and U.S. Pat. No. 5,154,842). The capsules are made by first emulsifying the liquid core material as small droplets in an aqueous phase comprising the melamine-formaldehyde or urea-formaldehyde resin, and then allowing the polymerisation reaction to proceed along with precipitation at the oil-water interface.

In some examples, the microcapsules may be prepared by a process comprising:

(i) providing a non-aqueous phase comprising the liquid core material;

(ii) providing an aqueous phase comprising a melamine-formaldehyde pre-polymer (e.g. a partially methylated methylol melamine resin);

(iii) emulsifying the non-aqueous and aqueous phases to form an emulsion comprising droplets of the non-aqueous phase dispersed in the aqueous phase; and (iv) condensing the melamine-formaldehyde pre-polymer, thereby forming a melamine-formaldehyde polymer which precipitates from the aqueous phase and encapsulates said droplets.

The polymerisation process is preferably performed using an emulsifier, which is preferably present in the aqueous phase. By way of illustration, an anionic emulsifier (e.g. copolymers of butyl acrylate and acrylic acid) and/or a neutral emulsifier (e.g. PVP) may be used.

Condensation of the melamine-formaldehyde pre-polymer may be initiated by, e.g., lowering the pH of the emulsion. The pH of the emulsion may be adjusted using a base as appropriate. Examples of suitable bases include alkali metal hydroxides (e.g. sodium hydroxide), ammonia, and triethanolamine.

In each of the emulsification processes described herein, emulsification can be conducted using any suitable mixing device known in the art. For example, a homogeniser, colloid mill, ultrasonic dispersion device, or ultrasonic emulsifier may be used. Preferably, a homogeniser is used.

The resulting polymeric shell may have a thickness of greater than 0.5 nm, preferably greater than 1 nm, and more preferably greater than 2 nm Typically, the polymeric shell will have a shell thickness of less than 2000 nm, preferably less than 1500 nm, and more preferably less than 1100 nm. The microcapsules preferably have a polymeric shell with a thickness of from 1 to 2000 nm, such as from 2 to 1100 nm Factors such as the concentration of the shell-forming material in the emulsion will dictate the thickness of the polymeric shell.

The size of the microcapsules can be controlled by altering factors such as the stirring speed and the shape of the stirring blade or rotor blade of the stirrer or homomixer used during the emulsification step of the microencapsulation process, or by adjusting the reaction rate by altering the polymerisation conditions (e.g. the reaction temperature and time) for the polymeric material. In particular, the size of the microcapsules may be controlled by regulating the stirring speed, which in turn regulates the size of the droplets of the liquid core material in the emulsion.

Metallic Coating

The coated microcapsules may further comprise a metallic coating which surrounds the microcapsules. The metallic coating has a maximum thickness of 1000 nm and comprises particles of a first metal adsorbed on the polymeric shell and a film of a second metal disposed on said particles. The film of the second metal provides for a continuous coating which surrounds the surface of the microcapsule. Preferably the thickness of the metallic coating is substantially uniform throughout the coating.

The particles of the first metal are preferably nanoparticles. The term "nanoparticles" as used herein refers to particles having a particle size of from 1 to 200 nm Preferably, the metal nanoparticles have a particle size of less than 100 nm, e.g. less than 50 nm More preferably, the metal nanoparticles have a particle size of less than 10 nm, more preferably less than 5 nm, and more preferably less than 3 nm. In this regard, the use of smaller metal nanoparticles may result in the formation of a thinner metallic coating. The nanoparticles will typically have a spheroidal geometry, but they may exist in more complex forms such as rods, stars, ellipsoids, cubes or sheets.

In some examples, the nanoparticles comprise gold, silver, copper, tin, cobalt, tungsten, platinum, palladium, nickel, iron or aluminium nanoparticles, or mixtures thereof. In some examples, the nanoparticles comprise an alloy of two or more metals, e.g. an alloy of two or more metals selected from gold, silver, copper, tin, cobalt, tungsten, platinum, palladium, nickel, iron and aluminium. In some examples, the nanoparticles comprise a metal oxide, e.g. aluminium oxide or an iron oxide. In some examples, the nanoparticles comprise core-shell particles comprising a core of a first metal or metal oxide surrounded by a shell of a second metal or metal oxide. In some examples, the nanoparticles consist of a single metal.

As described in more detail below, the film of the second metal is preferably applied by an electroless plating procedure which is catalysed by the particles of the first metal. It is therefore preferred that the particles of the first metal comprise a metal which catalyses the electroless plating process.

The first metal may be selected from the transition metals and p-block metals, e.g. a metal selected from those metals listed in Groups 9 to 14 of the Periodic Table, in particular a metal selected from Groups 10, 11 and 14. Preferably, the first metal is a metal selected from nickel, palladium, platinum, silver, gold, tin and combinations thereof. Preferably, the first metal comprises platinum, silver, gold, or a mixture thereof.

The first and second metals may be the same or different. Preferably, the second metal is different to the first metal.

The second metal is preferably a metal that is capable of being deposited via an electroless plating process. The second metal may be a transition metal, e.g. a metal selected from those metals listed in Groups 9 to 14 of the Periodic Table, in particular a metal selected from Groups 10 and 11. Preferably, the second metal is a metal selected from silver, gold, copper and combinations thereof.

In some examples, the first metal is selected from Au, Pt, Pd, Sn, Ag and combinations thereof; and the second metal is selected from Au, Ag, Cu, Ni and combinations thereof.

In some examples, the first metal is selected from Au, Pt, Pd, Sn, Ag and combinations thereof (e.g. Sn/Ag) and the second metal is Au. In some examples, the first metal is selected from Sn, Pt, Ag, Au and combinations thereof (e.g. Pt/Sn) and the second metal is Ag. In some examples, the first metal is selected from Sn, Ag, Ni and combinations thereof (e.g. Sn/Ni or Sn/Ag) and the second metal is Cu. In some examples, the first metal is selected from Sn, Pd, Ag and combinations thereof (e.g. Sn/Pd) and the second metal is Ni.

In some examples, the first metal is Pt and the second metal is Au; the first metal is Au and the second metal is Ag; or the first metal is Au and the second metal is Cu. More preferably, the first metal is Au and the second metal is Ag; or the first metal is Pt and the second metal is Au.

The particles of the first metal are preferably adsorbed onto the polymeric shell in the form of a discontinuous layer such that, prior to application of the metallic film, the surface of the polymeric shell comprises regions comprising adsorbed metal particles and regions in which adsorbed metal particles are absent. The metal particles may be distributed over the surface of the polymeric shell in a substantially uniform manner.

The thickness of the film of the second metal may vary with the density of the particles of the first metal that are adsorbed onto the polymeric shell of the microcapsule, with a higher density of particles of the first metal typically encouraging the growth of a thinner film. In some examples, the particles are deposited onto the polymeric shell at a density such that said particles cover from 0.1 to 80% of the surface area of the polymeric shell, e.g. from 0.5 to 40% of the surface area of the polymeric shell, e.g. from 1 to 4% of the surface area of the polymeric shell. The density of the particles on the polymeric shell may be determined using the procedure described in the Test Methods section herein.

The particles of the first metal are preferably adsorbed onto the polymeric shell by: (i) adsorbing charge-stabilised nanoparticles of the first metal onto the polymeric shell; (ii) adsorbing sterically-stabilised nanoparticles of the first metal onto the polymeric shell; or (iii) adsorbing particles of the first metal which are formed by reduction in situ. These methods are described in more detail below.

Deposition of the First Metal: Adsorption of Charge-Stabilised Nanoparticles

In some examples, the particles of the first metal are charge-stabilised nanoparticles which are adsorbed on the polymeric shell. Charge-stabilised nanoparticles are nanoparticles which comprise a charged species adsorbed on the surface thereof. Since the stabiliser is a charged species, it will impart a charged surface to the nanoparticles which can be exploited in order to adsorb the metal particles to the surface of the polymeric shell. In some examples, the particles of the first metal are adsorbed on the polymeric shell by electrostatic interaction.

The particles are preferably adsorbed on a surface-modifying agent that forms part of the polymeric shell. The surface-modifying agent may be adsorbed on and/or absorbed within the polymeric shell. Preferably, the polymeric shell was obtained by an emulsification process in which the surface-modifying agent was employed as an emulsifier, with the emulsifier being retained in the resulting shell. The surface-modifying agent preferably presents a charged surface which is used to electrostatically attract and adsorb the charge-stabilised nanoparticles on to the polymeric shell.

In some examples, the particles of the first metal are charge-stabilised by an anionic stabiliser. In some examples, the anionic stabiliser is selected from borohydride anions and citrate anions. In some examples, the anionic stabiliser is an anionic surfactant, e.g. an anionic surfactant selected from sodium dodecyl sulfate, sodium laureth sulfate, dodecyl benzene sulfonic acid, perfluorooctanesulfonate, dioctyl sodium sulfosuccinate and sodium stearate. Preferably, the particles are borohydride-stabilised or citrate-stabilised nanoparticles.

In some examples, the particles of the first metal have a zeta potential of from −20 mV to −150 mV, e.g. from −30 mV to −90 mV.

Where the particles of the first metal are stabilised by an anionic stabiliser, it is preferable for the surface of the polymeric shell to be neutral or cationic. In some examples, the polymeric shell has a substantially neutral surface having a zeta potential of from −10 mV to +10 mV, e.g. from −5 mV to +5 mV. In some examples, the polymeric shell has a positively charged surface, e.g. having a zeta potential of from +20 mV to +150 mV, e.g. from +30 mV to +90 mV.

In some examples, the particles of the first metal are stabilised by an anionic stabiliser and the polymeric shell comprises a non-ionic surface-modifying agent. In some examples, the surface-modifying agent is a non-ionic polymer, e.g. a non-ionic polymer selected from poly(vinyl alcohol) and poly(vinyl pyrrolidone).

In some examples, the particles of the first metal are stabilised by an anionic stabiliser and the polymeric shell comprises a cationic surface-modifying agent. The surface-modifying agent may be a cationic surfactant or a cationic polymer. Examples of cationic surfactants include, without limitation, alkyl ammonium surfactants such as cetyl trimethylammonium bromide, dodecyl dimethylammonium bromide, cetyl trimethylammonium chloride, benzalkonium chloride, cetylpyridinium chloride, dioctadecyl dimethylammonium chloride and dioctadecyl dimethylammonium bromide. Examples of cationic polymers include, without limitation, poly(diethylaminoethyl methacrylate), poly(dimethylaminoethyl methacrylate), poly(tertiarybutylaminoethyl methacrylate) and di-block copolymers formed of a first block comprising a poly(aminoalkyl acrylate) and a second block comprising a poly(alkyl acrylate). More preferably, the surface-modifying agent is cetyl trimethylammonium bromide.

Alternatively, the particles of the first metal may be charge-stabilised by a cationic stabiliser. Examples of cationic stabilisers include cationic surfactants such as quaternary ammonium surfactants, e.g. cetyl trimethylammonium bromide, tetraoctylammonium bromide and dodecyl trimethylammonium bromide. Other quaternary ammonium surfactants include the esterquats, i.e. quaternary ammonium surfactants containing an ester group.

In some examples, the particles of the first metal have a zeta potential of from +20 mV to +150 mV, e.g. from +30 mV to +90 mV.

Where the particles of the first metal are stabilised by a cationic stabiliser, it is preferable for the surface of the polymeric shell to be neutral or anionic. In some examples, the polymeric shell has a substantially neutral surface having a zeta potential of from −10 mV to +10 mV, e.g. from −5 mV to +5 mV. In some examples, the polymeric shell has a positively charged surface, e.g. having a zeta potential of from −20 mV to −150 mV, e.g. from −30 mV to −90 mV.

In some examples, the particles of the first metal are stabilised by a cationic stabiliser and the polymeric shell comprises a non-ionic surface-modifying agent. In some examples, the surface-modifying agent is a non-ionic polymer, e.g. a non-ionic polymer selected from poly(vinyl alcohol) and poly(vinylpyrrolidone).

In some examples, the particles of the first metal are stabilised by a cationic stabiliser and the polymeric shell comprises an anionic surface-modifying agent. The surface-modifying agent may be an anionic surfactant or an anionic polymer. Examples of anionic surfactants include, without limitation, sodium dodecyl sulfate, sodium laureth sulfate, dodecyl benzene sulfonic acid, dioctyl sodium sulfosuccinate, perfluorooctanesulfonate, dioctyl sodium sulfosuccinate and sodium stearate. Examples of anionic polymers include, without limitation, polyacids such as poly(acrylic acid) and poly(methacrylic acid).

The particles of the first metal may alternatively be charge-stabilised by a zwitterionic stabiliser. In some examples, the zwitterionic stabiliser is a zwitterionic surfactant. Examples of zwitterionic surfactants include aminobetaines, imidazoline derivatives and phospholipids, e.g. phosphatidyl cholines.

The charge-stabilised nanoparticles may be prepared using suitable procedures known in the art (see, e.g., G. Frens, Nature, 1973, 241, 20-22). Such procedures will typically involve reducing metal ions in solution in the presence of charged stabiliser. Thus, the charge-stabilised nanoparticles may be obtained by providing a solution comprising ions of the first metal and a charged stabiliser, and reducing the ions to form metal particles which are charge-stabilised by the stabiliser.

In some examples, metal ions in solution are reduced by a reducing agent which becomes the charged stabiliser e.g. by sodium borohydride or by sodium citrate. By way of illustration, and without limitation, borohydride-stabilised gold nanoparticles may be prepared by contacting an aqueous solution of chloroauric acid with sodium borohydride.

The resulting charge-stabilised nanoparticles may then be contacted with uncoated microcapsules under appropriate conditions, e.g. at ambient temperature. The microcapsules may then be washed to remove any unbound particles.

Preferably, the ions of the first metal are present in the solution at a concentration of from 0.005 to 50 mM, e.g. from 0.01 to 20 mM, e.g. from 0.05 to 5 mM. Preferably, the charged stabiliser is present in the solution at a concentration of from 0.005 to 50 mM, e.g. from 0.01 to 20 mM, e.g. from 0.05 to 5 mM.

Deposition of the First Metal: Adsorption of Sterically-Stabilised Nanoparticles In some examples, the first metal is deposited by adsorbing sterically-stabilised nanoparticles of the first metal onto the surface of the polymeric shell. Sterically-stabilised nanoparticles generally comprise a polymer or other macromolecule which is adsorbed on the surface of the metal particles, forming a protective sheath around the particles and minimising aggregation. The size of the steric stabiliser can be exploited in order to adsorb the metal particles onto the surface of the polymeric shell. In some examples, the particles of the first metal are adsorbed on the polymeric shell by steric interaction.

In some examples, the nanoparticles are sterically-stabilised by a polymeric stabiliser. Preferably, the polymer comprises one or more groups selected from carboxyl, hydroxyl, amine, and ester groups. The polymer may be a homopolymer or a copolymer (e.g. a graft copolymer or a block copolymer). Examples of suitable polymers include poly(ethylene oxide), polyethylene glycol, poly(acrylic acid), poly(acrylamide), poly(ethylene imine), poly(vinyl alcohol), carboxymethyl cellulose, chitosan, guar gum, gelatin, amylose, amylopectin, and sodium alginate.

Preferably the polymeric stabiliser has a weight average molecular weight of at least 5 kDa, more preferably at least 10 kDa, more preferably at least 20 kDa. Preferably, the molecular weight of the polymeric stabiliser is from 5 to 100 kDa, more preferably from 10 to 80 kDa, more preferably from 20 to 40 kDa.

In some examples, the polymeric stabiliser is a non-ionic polymer. Examples of non-ionic polymers include, without limitation, poly(vinyl alcohol), poly(vinyl propylene), poly(ethylene glycol) and poly(vinyl pyrrolidone). Poly(vinyl pyrrolidone) is particularly preferred as a steric stabiliser.

In some examples, the polymeric stabiliser is a cationic polymer. Examples of cationic polymers include, without limitation, poly(allyl amine) polymers, e.g. poly(allyl amine hydrochloride).

In some examples, the polymeric stabiliser is an anionic polymer. Examples of anionic polymers include, without limitation, polyacids, e.g. poly(acrylic acid) or poly(methacrylic acid).

In some examples, the nanoparticles are sterically-stabilised by a polymeric surfactant. Examples of suitable surfactants include, without limitation, polyoxyalkylene glycol alkyl ethers (e.g. polyoxyethylene glycol alkyl ethers and polyoxypropylene glycol alkyl ethers), sorbitan esters (e.g. polysorbates), fatty acid esters, poly(isobutenyl) succinic anhydride amine derivatives and amine oxides.

As with the polymeric stabiliser, the polymeric surfactant preferably has a weight average molecular weight of at least 5 kDa, more preferably at least 10 kDa, more preferably at least 20 kDa. Preferably, the polymeric surfactant has a weight average molecular weight of from 5 to 100 kDa, more preferably from 10 to 80 kDa, more preferably from 20 to 40 kDa.

The particles are preferably adsorbed on a surface-modifying agent that forms part of the polymeric shell. The surface-modifying agent may be adsorbed on and/or absorbed within the polymeric shell. Preferably, the polymeric shell was obtained by an emulsification process in which the surface-modifying agent was employed as an emulsifier, with the emulsifier being retained in the resulting shell. The sterically-stabilised nanoparticles preferably bind via steric interactions to the surface-modifying agent.

In some examples, the surface-modifying agent is a non-ionic surface-modifying agent, e.g. a non-ionic surfactant or a non-ionic polymer. Examples of non-ionic polymers include, without limitation, poly(vinyl alcohol) and poly(vinyl pyrrolidone). More preferably, the non-ionic polymer is poly(vinyl alcohol).

In some examples, the surface-modifying agent is a cationic surface-modifying agent, e.g. a cationic surfactant or a cationic polymer. Examples of cationic surfactants include, without limitation, cetyl trimethylammonium bromide, dodecyl dimethylammonium bromide, cetyl trimethylammonium chloride, benzalkonium chloride, cetylpyridinium chloride, dioctadecyl dimethylammonium chloride and dioctadecyl dimethylammonium bromide. Preferably, the cationic surface-modifying agent is cetyl trimethylammonium bromide.

In some examples, the surface-modifying agent is an anionic surface-modifying agent, e.g. an anionic surfactant or an anionic polymer. Examples of anionic surfactants include, without limitation, sodium dodecyl sulfate, sodium laureth sulfate, dodecyl benzene sulfonic acid, dioctyl sodium sulfosuccinate, perfluorooctanesulfonate, dioctyl sodium sulfosuccinate and sodium stearate. Examples of anionic polymers include, without limitation, polyacids such as poly(acrylic acid) and poly(methacrylic acid).

Suitable procedures for preparing the sterically-stabilised nanoparticles are known in the art (see, e.g., Horiuchi et al., Surface and Coatings Technology, 2010, 204, 3811-3817). By way of illustration, sterically-stabilised nanoparticles may be prepared by reducing metal ions in solution in the presence of a stabiliser.

Thus, in some examples, the sterically-stabilised nanoparticles are obtained by providing a solution comprising ions of the first metal and a stabiliser, and reducing the ions to form metal particles which are sterically-stabilised by the stabiliser. Preferably, the ions of the first metal are present in the solution at a concentration of from 0.01 to 100 mM, e.g. from 0.05 to 50 mM, e.g. from 0.1 to 10 mM. Preferably, the stabiliser is present in the solution at a concentration of from 0.0001 to 1 mM, e.g. from 0.005 to 0.5 mM, e.g. from 0.001 to 0.1 mM.

The particles of the first metal may be adsorbed on to the polymeric shell of the microcapsule by contacting the microcapsule with a slurry comprising said particles. Preferably, the metal nanoparticles are present in the slurry in an amount of more than 0.2% by weight and the slurry comprises less than 0.01% by weight of unbound stabiliser.

The contacting may take place under ambient conditions. However, in order to facilitate adsorption of the particles onto the microcapsule surface, the microcapsules may be heated so as to enhance penetration of the sterically-stabilised particles within the polymeric shell. Preferably, the microcapsules are heated to a temperature of from 30° C. to 80° C., e.g. from 40° C. to 70° C. In some examples, the polymeric shell comprises an amorphous polymer and the microcapsule is heated to a temperature above standard ambient temperature but below the glass transition temperature ($T_g$) of the polymer. Preferably, the elevated temperature is no more than 30° C. below, e.g. no more than 20° C. below, the glass transition temperature of the amorphous polymer. Examples of amorphous polymers include, without limitation, polyacrylates, e.g. poly(methyl methacrylate) and poly(ethyl methacrylate). The glass transition temperature of the polymer may be determined by differential scanning calorimetry (DSC) following ASTM E1356 ("Standard Test Method for Assignment of the Glass Transition Temperature by Differential Scanning calorimetry").

Deposition of the First Metal: Deposition by Reduction In Situ

In some examples, the particles of the first metal are adsorbed on to the polymeric shell by contacting the uncoated microcapsule with a solution comprising ions of the first metal and a reducing agent. The presence of the reducing agent causes the ions of the first metal to be reduced in situ. As the metal ions are reduced, they precipitate from the solution as metal particles and seek to lower the energy of the system by adsorbing onto the polymeric shell of the microcapsule. The first metal may also be adsorbed onto the polymeric shell of the microcapsule during the deposition process in the form of ions which have not been reduced by the reducing agent.

The reducing agent that is contacted with the uncoated microcapsule is preferably in solution. More preferably, the reducing agent is added to a solution comprising the metal ions and the uncoated microcapsule. Thus, deposition of the metal particles on the microcapsule surface may be achieved by preparing an aqueous solution comprising ions of the first metal and uncoated microcapsules. A reducing agent is then added to the solution, resulting in reduction of the metal ions and the precipitation of particles of the first metal onto the surface of the microcapsules. The reaction is allowed to progress for a time sufficient to allow the desired deposition of the metal particles on the microcapsule surface. The capsules may then be washed, separated from the other reagents and redispersed in water. The deposition process may be carried out at room temperature.

Preferably, the ions of the first metal are present in the solution at a concentration of from 0.005 to 50 mM, e.g. from 0.01 to 20 mM, e.g. from 0.05 to 5 mM. Preferably, the reducing agent is present in the solution at a concentration of from 0.05 to 500 mM, e.g. from 0.1 to 200 mM, e.g. from 0.5 to 50 mM.

The particles are preferably adsorbed on a surface-modifying agent that is present in the polymeric shell. The surface-modifying agent may be adsorbed on and/or absorbed within the polymeric shell. Preferably, the polymeric shell was obtained by an emulsification process in which the surface-modifying agent was employed as an emulsifier, with the emulsifier being retained in the resulting shell. The particles of the first metal may be adsorbed to the polymeric shell by one or more interactions selected from steric interactions and electrostatic interactions.

In some examples, the surface-modifying agent is a non-ionic surface-modifying agent, e.g. a non-ionic polymer. Examples of non-ionic polymers include, without limitation, poly(vinyl alcohol) and poly(vinyl pyrrolidone). More preferably, the non-ionic polymer is poly(vinyl alcohol).

In some examples, the surface-modifying agent is a cationic surface-modifying agent, e.g. a cationic surfactant or a cationic polymer. Examples of cationic surfactants include, without limitation, cetyl trimethylammonium bromide, dodecyl dimethylammonium bromide, cetyl trimethylammonium chloride, benzalkonium chloride, cetylpyridinium chloride, dioctadecyl dimethylammonium chloride and dioctadecyl dimethylammonium bromide. Preferably, the surface-modifying agent is cetyl trimethylammonium bromide.

In some examples, the surface-modifying agent is an anionic surface-modifying agent, e.g. an anionic surfactant or an anionic polymer. Examples of anionic surfactants include, without limitation, sodium dodecyl sulfate, sodium laureth sulfate, dodecyl benzene sulfonic acid, dioctyl sodium sulfosuccinate, perfluorooctanesulfonate, dioctyl sodium sulfosuccinate and sodium stearate. Examples of anionic polymers include, without limitation, polyacids such as poly(acrylic acid) and poly(methacrylic acid).

Deposition of the Second Metal

Once the particles of the first metal have been adsorbed onto the polymeric shell, a film of a second metal is formed on the particles of the first metal, thereby coating the polymeric shell with a continuous metallic film that surrounds the microcapsule. Preferably the thickness of the metallic coating is substantially uniform throughout the coating.

The metallic film is preferably formed by an electroless plating process in which the deposition of the second metal is catalysed by the adsorbed particles of the first metal. The electroless deposition process will generally comprise contacting microcapsules onto which particles of the first metal have been deposited with a solution of ions of the second metal in the presence of a reducing agent, in the absence of an electric current. The reducing agent is typically a mild reducing agent such as formaldehyde and the electroless plating is preferably performed under alkaline conditions. Once the electroplating reaction commences, the deposition of the metallic coating may become autocatalytic. The thickness of the metallic film may be controlled by limiting the concentration of the ions of the second metal in solution and/or the duration of the electroless plating procedure.

Suitable techniques for conducting the electroless plating procedure are described, for example, in the following documents: Basarir et al., ACS Applied Materials & Interfaces, 2012, 4(3), 1324-1329; Blake et al., Langmuir, 2010, 26(3), 1533-1538; Chen et al., Journal of Physical Chemistry C, 2008, 112(24), 8870-8874; Fujiwara et al., Journal of the Electrochemical Society, 2010, 157(4), pp. D211-D216; Guo et al., Journal of Applied Polymer Science, 2013, 127(5), 4186-4193; Haag et al., Surface and Coatings Technology, 2006, 201(6), 2166-2173; Horiuchi et al., Surface & Coatings Technology, 2010, 204(23), 3811-3817; Ko et al., Journal of the Electrochemical Society, 2010, 157(1), pp. D46-D49; Lin et al., International Journal of Hydrogen Energy, 2010, 35(14), 7555-7562; Liu et al., Langmuir, 2005, 21(5), 1683-1686; Ma et al., Applied Surface Science, 2012, 258(19), 7774-7780; Miyoshi et al., Colloids and Surfaces A: Physicochemical and Engineering Aspects, 2008, 321(1-3), 238-243; Moon et al., 2008, Ultramicroscopy, 108(10), 1307-1310; Wu et al., Journal of Colloid and Interface Science, 2009, 330(2), 359-366; Ye et al., Materials Letters, 2008, 62(4-5), 666-669; and Zhu et al., Surface and Coatings Technology, 2011, 205(8-9), 2985-2988.

By way of illustration, and without limitation, a silver film may be prepared by forming a dispersion comprising silver nitrate, formaldehyde, ammonia and microcapsules comprising particles of the first metal. The dispersion is then stirred for a sufficient period of time until a metallic film of the desired thickness is obtained. The capsules may then be washed, e.g. by centrifugation, in order to separate them from the plating solution.

The ions of the second metal are preferably present in the solution at a concentration of from 0.05 to 2000 mM, e.g.

from 0.1 to 1750 mM, e.g. from 0.5 to 1500 mM. Preferably, the reducing agent is present in the solution at a concentration of from 0.05 to 3500 mM, e.g. from 0.1 to 3000 mM, e.g. from 0.5 to 2500 mM. Preferably, the second metal and the reducing agent are present in the solution at a molar ratio of second metal to reducing agent of from 1:10 to 4:1, e.g. from 1:5 to 2:1, e.g. from 1:3 to 1:1.

The electroless plating process may be performed at any suitable temperature, e.g. a temperature of from 0 to 80° C. Preferably, the electroless plating process is performed at room temperature.

Characteristics and Properties of the Coated Microcapsules

The coated microcapsules may be obtained in a range of different particle sizes. Preferably, the coated microcapsules have a particle size of at least 0.1 microns, more preferably at least 1 micron. Typically, the coated microcapsules will have particle size of 500 microns or less, such as 100 microns or less, and more preferably 50 microns or less. Preferably, the coated microcapsules have a particle size of from 0.1 to 500 microns, e.g. from 1 to 100 microns, e.g. from 1 to 30 microns, e.g. from 1 to 20 microns. The particle size of the coated and uncoated microcapsules may be determined using the test procedure described in the Test Methods section herein.

The coated microcapsules comprise a metallic coating having a maximum thickness of 1000 nm. The thickness of the metallic coating may be chosen such that the coated microcapsules rupture and release the encapsulated liquid core material under particular conditions, e.g. under particular stresses. For instance, when the coated microcapsules comprise a perfume oil and form part of a fragrance formulation that is worn by a user, the metallic coating may rupture during use, e.g. due to rubbing of the skin to which the formulation has been applied. In this way, the perfume oil may be released in a controlled manner so that it is perceptible to the user for a prolonged period of time.

Conversely, it is also desirable for the metallic coating to have a minimum thickness so as to reduce the likelihood of solvents permeating through the microcapsule wall and/or the metallic coating rupturing prematurely when the coated microcapsules are stored, transported or used. This is particularly important in the case of fine fragrance formulations, which will typically comprise a polar solvent such as ethanol in which the microcapsules are dispersed.

In some examples, the metallic coating has a maximum thickness of 500 nm, e.g. a maximum thickness of 400 nm, e.g. a maximum thickness of 300 nm, e.g. a maximum thickness of 200 nm, e.g. a maximum thickness of 150 nm, e.g. a maximum thickness of 100 nm, e.g. a maximum thickness of 50 nm. In some examples, the metallic coating has a minimum thickness of 1 nm, e.g. a minimum thickness of 10 nm, e.g. a minimum thickness of 30 nm. In some examples, the metallic coating has: a minimum thickness of 1 nm and a maximum thickness of 500 nm; a minimum thickness of 10 nm and a maximum thickness of 300 nm; or a minimum thickness of 10 nm and a maximum thickness of 200 nm Preferably, the metallic coating has: a minimum thickness of 10 nm and a maximum thickness of 150 nm; a minimum thickness of 10 nm and a maximum thickness of 100 nm; a minimum thickness of 20 nm and a maximum thickness of 100 nm.

The coated microcapsules are designed to release their liquid core material when the microcapsules are ruptured. The rupture can be caused by forces applied to the shell during mechanical interactions. The microcapsules may have a fracture strength of from about 0.1 MPa to about 25 MPa. The microcapsules preferably have a fracture strength of at least 0.5 MPa. So that the microcapsules are readily friable, they preferably have a fracture strength of less than 25 MPa, more preferably of less than 20 MPa, more preferably of less than 15 MPa. For instance, the microcapsules may have a fracture strength of from 0.5 to 10 MPa. The fracture strength of the microcapsules may be measured according to the Fracture Strength Test Method described in WO 2014/047496 (see pages 28-30 thereof).

The coated microcapsules may be characterised in terms of their permeability. A coated microcapsule may retain more than 50% by weight of the liquid core material under the Ethanol Stability Test described herein. More preferably, the coated microcapsule preferably retains more than 70% by weight of the liquid core material, e.g. more than 80% by weight, e.g. more than 85% by weight, e.g. more than 90% by weight, e.g. more than 95% by weight, e.g. more than 98% by weight, when tested under the Ethanol Stability Leakage Test described herein.

In some examples, the metallic coating is applied to an uncoated microcapsule which would otherwise retain less than 20% by weight of its liquid core material when tested under the Ethanol Stability Leakage Test described herein, e.g. less than 10%, e.g. less than 5%, e.g. less than 1%.

Formulations and Uses

The coated microcapsules will typically be formulated as a plurality of coated microcapsules. Thus, formulations may comprise a plurality of the coated microcapsules disclosed herein. The coated microcapsules will typically be dispersed in a solvent. For example, the coated microcapsules may be dispersed in water or a polar solvent, e.g. an alcohol such as ethanol.

Preferably, the formulation comprises the coated microcapsules in an amount of at least 1% by weight of the formulation. For example, the coated microcapsules may be present in an amount of at least 5% by weight, at least 7% by weight or at least 10% by weight of the formulation. The formulation may comprise a mixture of different coated microcapsules of the present disclosure, the mixture comprising a plurality of coated microcapsules comprising a first liquid core material and a plurality of coated microcapsules comprising a second liquid core material. Alternatively or additionally, the formulation may comprise other microcapsules, e.g. uncoated microcapsules, in addition to the coated microcapsules disclosed herein.

Preferably, at least 75%, 85% or even 90% by weight of the coated microcapsules in the formulation have a particle size of from 1 microns to 100 microns, more preferably from 1 microns to 50 microns, even more preferably from 10 microns to 50 microns, most preferably from 1 microns to 30 microns. Preferably, at least 75%, 85% or even 90% by weight of the coated microcapsules have a polymeric shell thickness of from 60 nm to 250 nm, more preferably from 80 nm to 180 nm, even more preferably from 100 nm to 160 nm.

The coated microcapsules may be used in a wide variety of consumer products. Thus, the coated microcapsules may be used in products for baby care, beauty care, fabric care, home care, family care, feminine care or health care.

Preferably, the coated microcapsules are used in topically applied products, including fine fragrances and skin care products, including shaving products. The coated microcapsules disclosed herein may be used in consumer products (i.e. products intended to be sold to consumers without further modification or processing). Non-limiting examples of consumer products useful herein include products for treating hair (human, dog, and/or cat), including, bleaching, coloring, dyeing, conditioning, growing, removing, retarding growth, shampooing, styling; deodorants and antiperspirants; personal cleansing; color cosmetics; products, and/or methods relating to treating skin (human, dog, and/or cat), including application of creams, lotions, and other topically applied products for consumer use; and products and/or methods relating to orally administered materials for enhancing the appearance of hair, skin, and/or nails (human, dog, and/or cat); shaving; body sprays; and fine fragrances like colognes and perfumes; products for treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products relating to disposable absorbent and/or non-absorbent articles including adult incontinence garments, bibs, diapers, training pants, infant and toddler care wipes; hand soaps, shampoos, lotions, oral care implements, and clothing; products such as wet or dry bath tissue, facial tissue, disposable handkerchiefs, disposable towels, and/or wipes; products relating to catamenial pads, incontinence pads, interlabial pads, panty liners, pessaries, sanitary napkins, tampons and tampon applicators, and/or wipes.

In particular, a fragrance formulation that comprises a plurality of coated microcapsules as disclosed, the coated microcapsules comprising a liquid core material comprising a perfume oil. The formulation may comprise a polar solvent in which the coated microcapsules are dispersed. In some examples, the polar solvent is ethanol. In some examples, the fragrance formulation comprises a plurality of coated microcapsules as disclosed herein dispersed in ethanol. In some examples, the fragrance formulation is a fine fragrance formulation.

Test Methods

Test Method for Measuring the Size of the Microcapsules

The dimensions of uncoated and coated microcapsules may be measured using a Malvern Mastersizer Hydro 2000SM particle size analyser. Measurements are performed according to British Standard BS ISO 13099-1:2012 ("Colloidal systems—Methods for zeta-potential determination").

Test Method for Measuring the Size of the Metal Particles

The dimensions of metal particles may be measured by dynamic light scattering. Specifically, a Malvern Nano-ZS Zetasizer and FEI Tecnai TF20 field emission transmission gun electron microscopy (FEGTEM) fitted with HAADF detector and Gatan Orius SC600A CCD camera may be used.

Test Method for Measuring the Thickness of the Polymeric Shell and the Metallic Coating The thickness of the polymeric shell and the metallic coating may be measured using microtoming and FEGTEM. In order to prepare capsule cross-section samples for TEM imaging, 1% of the washed capsules are centrifuged and redispersed in 1 mL of ethanol. The capsule samples are then air dried and mixed with EPO FIX epoxy resin. The sample is left to harden overnight and ~100 nm thick microtome samples are floated onto water and set on TEM grids. FEGTEM is used to generate images of the microtomes and the thickness of the polymeric shell and the metallic coating may be determined using a computer program, such as Image J.

Test Method for Measuring the Adsorption Density of Metal Particles on the Capsule Surface Metal particle surface adsorption densities may be measured directly from TEM images. Adsorption densities can be measured for small sample boxes on the surface of the capsule. The distance from the centre of the sphere is then noted in each case. Each measurement was then corrected for both surface curvature and halved to compensate for the transparent nature of the capsules (TEM imaging shows the metal particles on both sides of the capsule). The size distribution of the capsules is then used to convert the number density obtained from these images to a 2D surface coverage (percent).

Test Method for Measuring the Zeta Potentials of Uncoated Microcapsules, Metal Particles and Coated Microcapsules The zeta potentials of uncoated microcapsules, the metal particles and the coated capsules may be analysed using a Malvern nano-ZS zetasizer. Zeta potentials are measured according to British Standard BS ISO 13099-1:2012 ("Colloidal systems—Methods for zeta-potential determination").

Test Method for Analysing the Chemical Composition of the Coated Microcapsules

The chemical composition of the coated microcapsules may be analysed using an Oxford Instruments INCA 350 energy dispersive X-ray spectroscopy (EDX) with 80 mm X-Max SDD detector, which is installed in FEGTEM; and EDX in FEGTSEM.

Ethanol Stability Test

The Ethanol Stability Test refers to the following test procedure.

A known volume of microcapsules (coated or uncoated microcapsules) are isolated and dispersed in an aqueous solution consisting of 1 part water to 4 parts absolute ethanol. The dispersion is heated to 40° C. After 7 days at 40° C., the microcapsules are isolated from the aqueous solution using centrifugation at 7000 rpm for 1 minute.

The aqueous solution is then subjected to analysis using gas chromatography to determine the content of the liquid core material that has leached from the microcapsules. Samples are assessed using a fused silica column of 3 m in length and 0.25 mm internal diameter, coated with a 0.25 mm film of 100% dimethyl polysiloxane stationary phase. The column temperature is programmed to increase from 50° C. to 300° C. at a rate of 20° C. per minute. A Clarus 580 gas chromatograph is used for the analysis.

Where the loss of liquid core material from coated microcapsules is compared with that from uncoated microcapsules, the uncoated microcapsules may be subjected to the washing steps of the coating procedure, to ensure that there is equivalent liquid core material loss from the coated and uncoated microcapsules in advance of the Ethanol Stability Test.

To confirm the presence of the liquid core material within the coated microcapsules, a known sample of capsules is crushed between two glass slides and washed into a vial with 5 ml ethanol. The capsules are isolated from the aqueous solution using centrifugation at 7000 rpm for 1 minute. The aqueous solution is then subjected to analysis using gas chromatography to determine the content of the liquid core material that has leached from the microcapsules.

The following Examples describe and illustrate embodiments within the scope of the present invention. The Examples are given solely for the purpose of illustration and are not to be construed as limitations of the present invention, as many variations thereof are possible without departing from the spirit and scope of the invention.

Unless otherwise stated, the test procedures used in these Examples are those specified in the Test Methods section of this specification.

Example 1: Synthesis of Microcapsules Comprising a Polyacrylate Shell and an n-Hexadecane Core The following procedure was used to prepare microcapsules comprising a polyacrylate shell and an n-hexadecane core. Microcapsules were prepared by a coacervation procedure which involved oil-in-water emulsification followed by solvent extraction. Poly(vinyl alcohol) was used as an emulsifier.

2.5 g of poly(methyl methacrylate) (PMMA, 99%, Sigma) was dissolved in 70.5 g of dichloromethane (DCM) (>99%, Acros Organics). 5.0 g of n-hexadecane (99%, Acros Organics) was added to this and mixed until one phase formed. This formed the "core" phase. In a 100 ml volumetric flask, a 2% emulsifier solution was prepared by dissolving a sufficient amount of poly(vinyl alcohol) (PVA, 67 kDa, 8-88 Fluka) in Milli-Q water, to form the "continuous" phase. 7 ml of both the "core" and "continuous" phase was added to a glass vial and emulsified using a homogeniser (IKA T25 Ultra-Turrax) at 15000 rpm for 2 min. The stabilised emulsion was then stirred magnetically at 400 rpm while 86 ml of the "continuous" phase was poured in slowly. The diluted emulsion was then stirred at 400 rpm for 24 hours at room temperature to allow capsule formation to occur. The dispersion was transferred into a separating funnel and the capsules allowed to cream. The aqueous phase of excess PVA was removed, and replaced with Milli-Q water three times. The capsules were redispersed in 50 ml Milli-Q water.

Example 2: Synthesis of Microcapsules Containing a Polyacrylate Shell and a Toluene Core The following procedure was used to prepare microcapsules comprising a polyacrylate shell and a toluene core. Microcapsules were prepared by a coacervation procedure which involved oil-in-water emulsification followed by solvent extraction. Cetyl trimethylammonium bromide was used as an emulsifier.

5 g of poly(ethyl methacrylate) (PEMA, 99%, Sigma) was dissolved in 81 g of dichloromethane (DCM) (>99%, Acros Organics). 14 g of toluene (99%, Acros Organics) was added to this and mixed until one phase formed. This formed the "core" phase. In a 100 ml volumetric flask, a 0.28% emulsifier solution was prepared by dissolving a sufficient amount of cetyl trimethylammonium bromide (CTAB, 98%, Sigma) in Milli-Q water, to form the "continuous" phase. 7 ml of both the "core" and "continuous" phase was added to a glass vial and emulsified using a homogeniser (IKA T25 Ultra-Turrax) at 15000 rpm for 2 min. The stabilised emulsion was then stirred magnetically at 400 rpm while 86 ml of the "continuous" phase was poured in slowly. The diluted emulsion was then stirred at 400 rpm for 24 hours at room temperature to allow capsule formation to occur. The capsules were isolated by washing via centrifugation (Heraeus Megafuge R16) and removing the supernatant three times at 4000 rpm for 5 min. The capsules were redispersed in 25 ml Milli-Q water.

Example 3: Synthesis of Microcapsules Containing a Polyacrylate Shell and a Hexyl Salicylate Core The following procedure was used to prepare microcapsules comprising a polyacrylate shell and a hexyl salicylate core. Microcapsules were prepared by a coacervation procedure which involved oil-in-water emulsification followed by solvent extraction. Poly(vinyl alcohol) was used as an emulsifier.

10 g of poly(methyl methacrylate) (PMMA, 99%, Sigma) was dissolved in 60 g of dichloromethane (DCM) (>99%, Acros Organics). 30 g of hexyl salicylate (Procter and Gamble) was added to this and mixed until one phase formed. This formed the "core" phase. In a 100 ml volumetric flask, a 0.28% emulsifier solution was prepared by dissolving a sufficient amount of cetyl trimethylammonium bromide (CTAB, 98%, Sigma) in Milli-Q water, to form the "continuous" phase. 7 ml of both the "core" and "continuous" phase was added to a glass vial and emulsified using a homogeniser (IKA T25 Ultra-Turrax) at 15000 rpm for 2 min. The stabilised emulsion was then stirred magnetically at 400 rpm while 86 ml of the "continuous" phase was poured in slowly. The diluted emulsion was then stirred at 400 rpm for 24 hours at room temperature to allow capsule formation to occur. The capsules were isolated by washing via centrifugation (Heraeus Megafuge R16) and removing the supernatant three times at 4000 rpm for 5 min. The capsules were redispersed in 50 ml Milli-Q water.

Example 4: Preparation of Charge-Stabilised Gold Nanoparticles

The following procedure was used to prepare borohydride-stabilised gold nanoparticles.

0.34 g $HAuCl_4$ was dissolved in Milli-Q water in a 25 ml volumetric flask. 0.036 g HCl was dissolved in Milli-Q water in a 25 ml volumetric flask. The $HAuCl_4$ and HCl solutions were combined in a separate flask. 1.25 ml of this was added dropwise to 47.25 ml Milli-Q water and stirred vigorously. A borohydride solution was prepared by adding 0.095 g $NaBH_4$ dissolved in 25 ml Milli-Q water, to 0.1 g NaOH dissolved in 25 ml Milli-Q water. 1.5 ml of this was added all at once, and the solution was stirred for 1 minute. The solution changed colour from pale yellow to dark ruby red indicating formation of Au nanoparticles.

Example 5: Adsorption of Charge-Stabilised Gold Nanoparticles onto Microcapsules The following procedure was used to adsorb the charge-stabilised gold nanoparticles of Example 4 onto the surface of the microcapsules of Examples 2 and 3.

6 ml of the Au nanoparticles were added to a beaker and stirred vigorously. 0.5 ml microcapsules were added dropwise, and stirred vigorously for a further 10 minutes. The microcapsules were collected by centrifuging (Heraeus Megafuge R16) and removing the supernatant four times at 4000 rpm for 10 min, to remove excess nanoparticles, and were then redispersed in water (2 ml).

Example 6: Preparation of Sterically-Stabilised Platinum Nanoparticles

The following procedure was used to prepare poly(vinyl pyrrolidone)-stabilised platinum nanoparticles.

0.5 g of poly(vinyl pyrrolidone) (PVP, 40 kDa, Fluka) was dissolved in 250 ml Milli-Q water. 31.25 ml of this was added to a 1 L volumetric flask and filled to 1 L with Milli-Q water to give a 0.00625 wt % solution of PVP. 100 ml of this PVP solution was placed in a 250 ml conical flask and 0.23 g of $H_2PtCl_6.6H_2O$ was added and stirred to dissolve. A 0.5 mM solution of $NaBH_4$ was made by dissolving 0.189 g $NaBH_4$ in 10 ml Milli-Q water. 0.4 ml of this was added to the platinum salt-PVP solution with vigorous stirring for 2 minutes. The solution immediately turned dark brown and was left to stand overnight to form Pt-PVP nanoparticles.

Example 7: Adsorption of Sterically-Stabilised Platinum Nanoparticles onto Microcapsules The following procedure was used to adsorb the PVP-stabilised platinum nanoparticles of Example 6 onto the surface of the microcapsules of Examples 1-3.

2 ml of capsules were added to 5 ml of PVP-stabilised platinum nanoparticles in a 40 ml glass vial, and mixed on a carousel for 10 min. The capsules were then washed by centrifugation at 4000 rpm for 5 minutes, three times. The capsules were redispersed in 30 ml Milli-Q water.

Example 8: Adsorption of Platinum Nanoparticles onto Microcapsules Via Reduction In Situ The following procedure was used to adsorb platinum nanoparticles via reduction in situ onto the surface of the microcapsules of Examples 1-3.

In a 100 ml volumetric flask, 0.023 g of $H_2PtCl_6 \cdot 6H_2O$ was dissolved in Milli-Q water up to 100 ml. 50 ml of this was placed in a conical flask and 1.25 ml capsules was added and stirred vigorously for 30 min 0.075 g of $NaBH_4$ (Aldrich) was dissolved to 100 ml with Milli-Q water. 50 ml of this was added drop-wise. Vigorous stirring was continued for 30 min. The capsules were then washed by separation for 72 h, allowing the excess Pt to sediment and capsules to cream. The excess Pt and water was removed using a 50 ml pipette and the capsules were redispersed in 7.5 ml Milli-Q water.

Example 9: Formation of Silver Film by Electroless Plating

The following procedure was used to form a continuous silver film on the microcapsules of Example 5 by electroless plating.

2 ml of microcapsules were added to a beaker containing 47.5 ml Milli-Q water. 0.5 ml of 0.1M $AgNO_3$ (99%, Sigma) was added and stirred vigorously. Then 50 μl of formaldehyde (35% in $H_2O$, Sigma) was added, followed by 26 μl of ammonia (25% in $H_2O$, Sigma) to control the pH to ~10, giving a silver-grey dispersion. The dispersion was then stirred for 10 min after which it was centrifuged at 4000 rpm for 10 min, 3 times, for washing, replacing the supernatant each time with Milli-Q water.

Example 10: Formation of Gold Film by Electroless Plating

The following procedure was used to form a continuous gold film on the surface of the microcapsules of Examples 7 and 8 by electroless plating.

1.58 g of $HAuCl_4$ (99.9%, Sigma) was dissolved to 100 ml with Milli-Q water. 0.58 g of hydrogen peroxide (35% in water, Aldrich) was dissolved to 100 ml with Milli-Q water. 0.2 g of poly(vinyl pyrrolidone) was dissolved to 100 ml with Milli-Q water. 1 ml of each of the above solutions was added to a 40 ml glass vial to form the plating solution. 7.5 ml of the microcapsules was added dropwise to the plating solution and stirred vigorously for 5 min. The capsules were washed by centrifugation at 4000 rpm for 5 minutes, three times.

Example 11: Characterisation of Microcapsules Comprising a Pt/Au Metallic Coating Coated microcapsules comprising a PMMA shell, a hexadecane core and a metallic coating comprising a gold film disposed on a layer of platinum nanoparticles were prepared following the procedures described in Examples 1, 8 and 10. The coated microcapsules were then characterised using SEM and TEM.

Figure 2A:
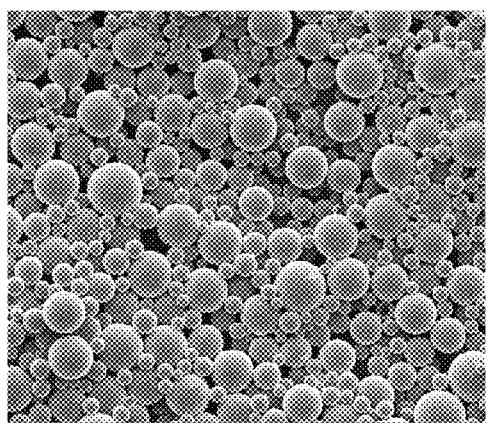
FIGS. 2A, 2B, and 2C provide SEM and TEM images obtained at various stages of preparation of a coated microcapsule comprising a poly(methyl methacrylate) (PMMA) shell, a hexadecane core and a metallic coating comprising a continuous gold film formed on a layer of platinum nanoparticles. Shown are.
Figure 2B:
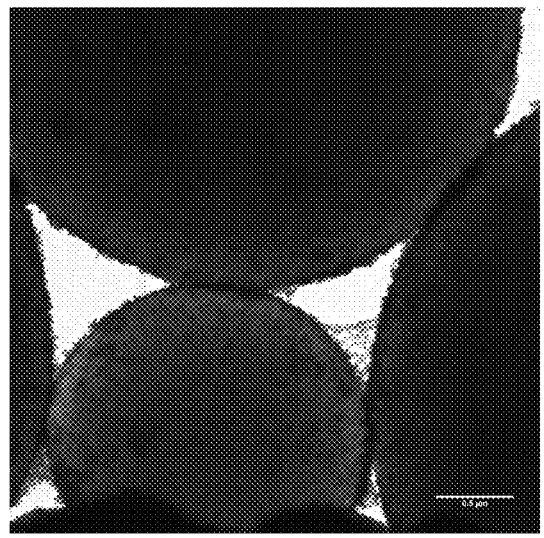
Figure 2C:
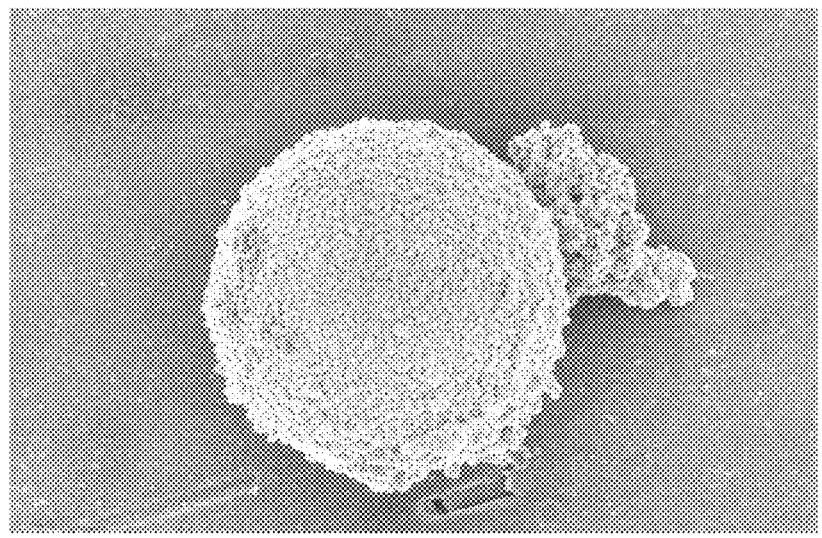

FIG. 2A is an SEM image of the uncoated PMMA microcapsules. FIG. 2B is a TEM image showing the platinum nanoparticles adsorbed on the outer surface of the PMMA microcapsules. FIG. 2C is an SEM image showing the continuous gold film. The maximum thickness of the metallic coating was less than 200 nm in this example, but it will be appreciated that the thickness of the coating may be varied.

Example 12: Characterisation of Microcapsules Comprising an Au/Ag Metallic Coating Coated microcapsules comprising a PEMA shell, a toluene core and a metallic coating comprising a silver film disposed on a layer of borohydride-stabilised gold nanoparticles were prepared following the procedures described in Examples 2, 4, 5 and 9. The coated microcapsules were then characterised using optical microscopy, SEM, TEM and EDX.

Figure 3D:
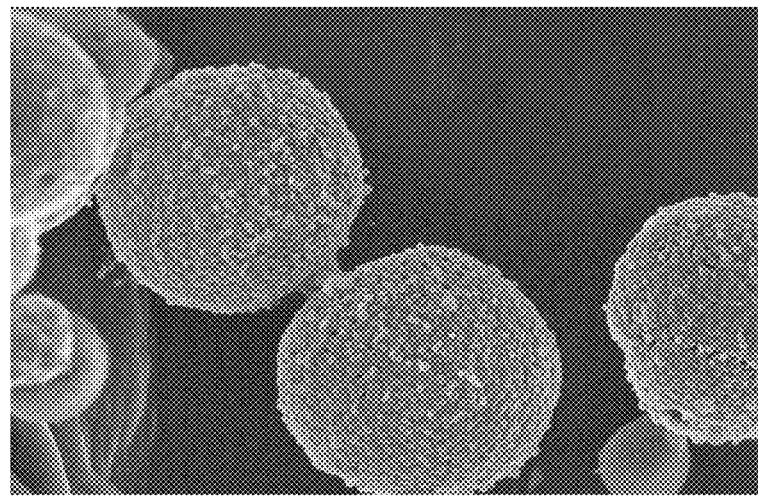
Figure 3E:
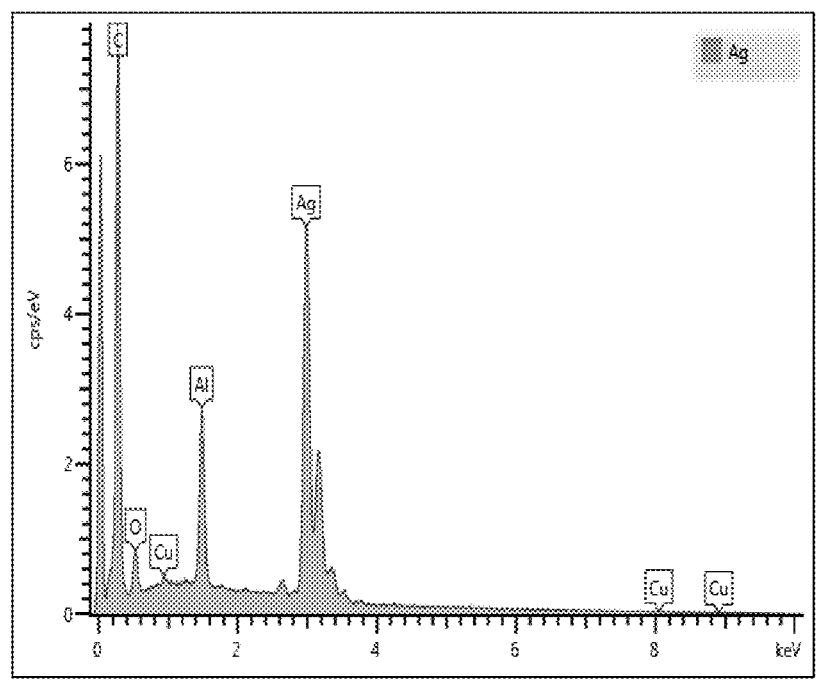
Figures 4A, 4B, 4C, 4D, 4E:
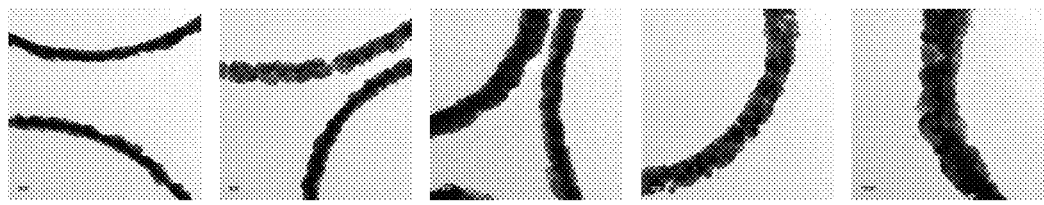
FIGS. 4A, 4B, 4C, 4D, and 4E are a series of TEM images showing metallic films of varying thicknesses.
Figure 5:
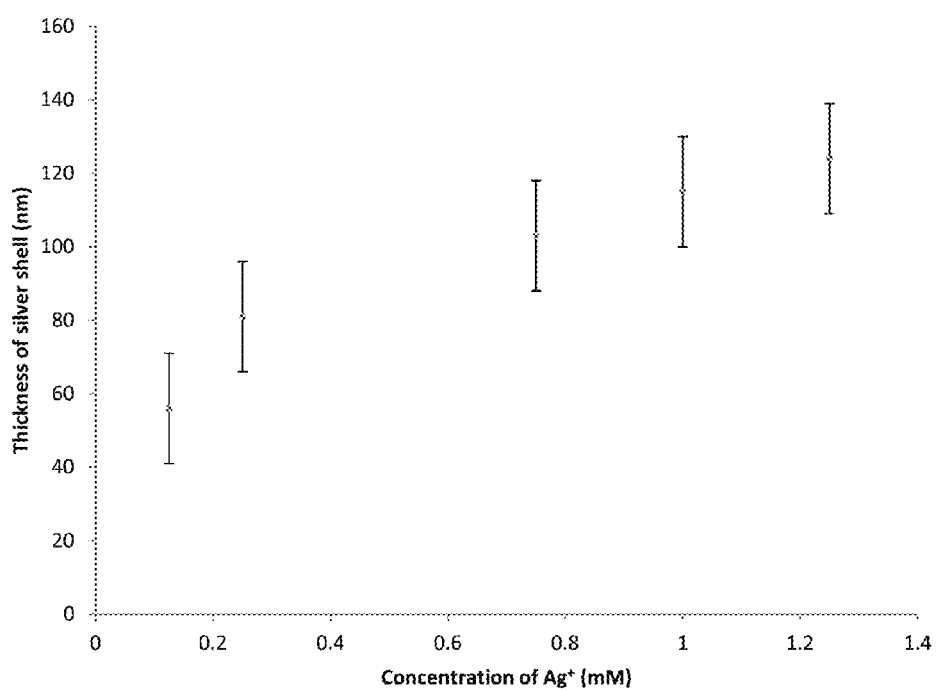
FIG. 5 is a graph which illustrates that the thickness of the metallic coating may be modified by varying the concentration of silver ions in the electroless plating solution.

FIG. 3A is an optical micrograph showing the uncoated PEMA microcapsules. FIG. 3B and FIG. 3C are a TEM image showing the borohydride-stabilised gold nanoparticles adsorbed on the surface of the microcapsules. FIG. 3D is an SEM image showing the continuous silver film. FIG. 3E is an EDX graph of the silver film. The maximum thickness of the metallic coating was 140 nm in this example, but it will be appreciated that the thickness of the coating may be varied. Reference is made in this regard to FIGS. 4A, 4B, 4C, 4D and 4E and 5, which illustrate that the thickness of the metallic coating may be modified by, for example, varying the concentration of silver ions in the electroless plating solution.

Example 13: Characterisation of Microcapsules Comprising a Pt/Au Metallic Coating Coated microcapsules comprising a PMMA shell, a hexyl salicylate core and a metallic coating comprising a gold film disposed on a layer of PVP-stabilised platinum nanoparticles were prepared following the procedures described in Examples 3, 6, 7 and 10. The coated microcapsules were then characterised using optical microscopy, SEM and TEM.

Figure 6A:
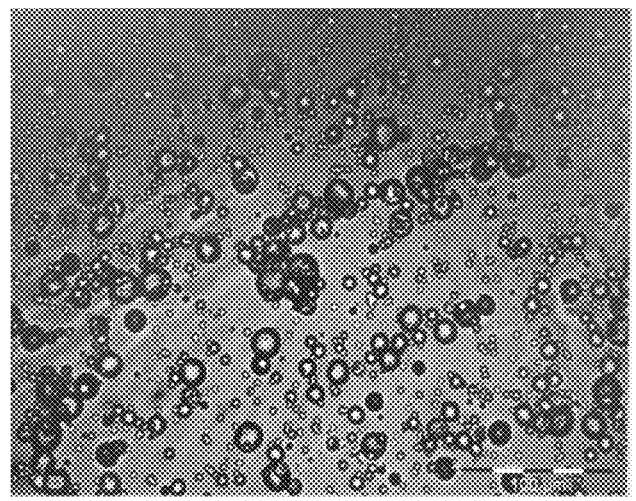
FIGS. 6A, 6B, and 6C provide optical, SEM and TEM images obtained at various stages of preparation of a coated microcapsule, the microcapsule comprising a PMMA shell, a hexyl salicylate core and a metallic coating comprising a layer of PVP-stabilised platinum nanoparticles and a continuous gold film disposed thereon. Shown are.
Figure 6B:
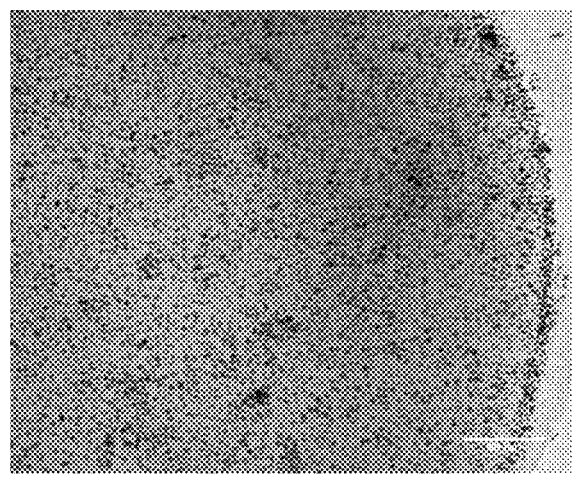
Figure 6C:
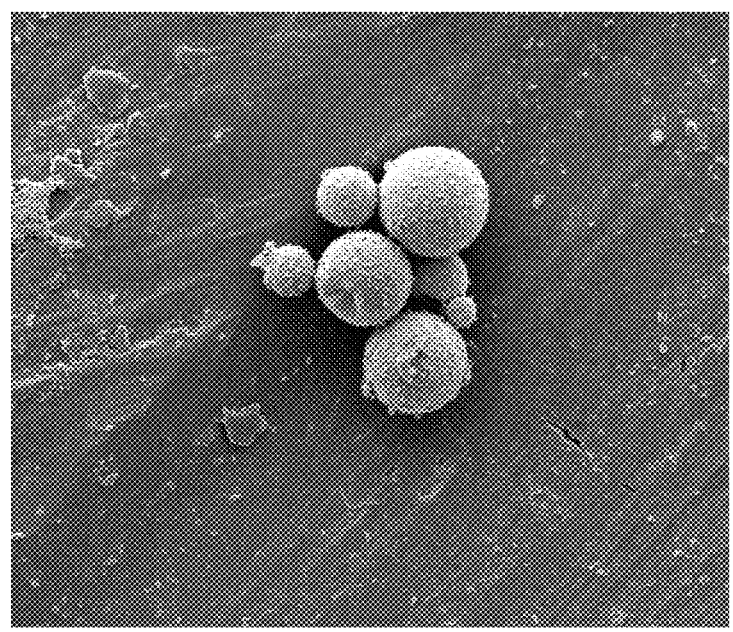

FIG. 6A is an optical micrograph showing the uncoated PMMA microcapsules. FIG. 6B is a TEM image showing the PVP-stabilised platinum nanoparticles adsorbed on the surface of the microcapsules. FIG. 6C is an SEM image showing the gold film on the microcapsules. The maximum thickness of the metallic coating was less than 100 nm in this example, but it will be appreciated that the thickness of the coating may be varied.

Example 14: Performance of Coated Microcapsules Under the Ethanol Stability Test Coated microcapsules comprising a PMMA shell, a hexadecane core and a metallic coating comprising a layer of platinum nanoparticles and a continuous gold film disposed thereon was prepared following the procedures described in Examples 1, 8 and 10. The coated microcapsules were then tested for their ability to retain the liquid core material using the Ethanol Stability Test described herein, and their performance was compared with that of uncoated PMMA microcapsules.

Figure 7A:
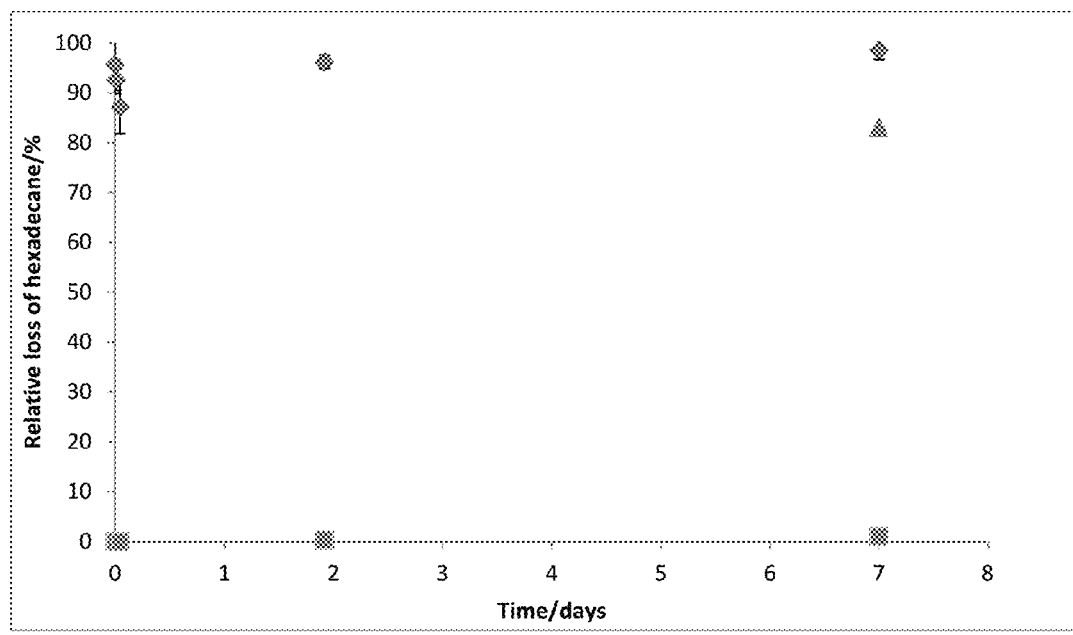
FIG. 7A is a graph showing the performance of coated PMMA microcapsules (data points indicated as squares) and uncoated PMMA microcapsules (data points indicated as diamonds) under the Ethanol Stability Test described herein. Also provided is a data point obtained after fracturing the coated PMMA microcapsules at the end of the experiment (see the data point indicated as a triangle).
Figure 7B:
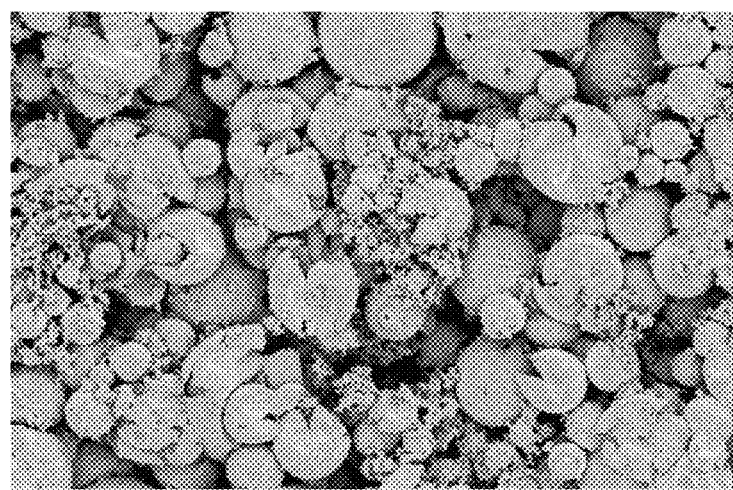
FIG. 7B is an SEM image showing the fractured microcapsules.

FIG. 7A is a graph showing the performance of the coated PMMA and uncoated PMMA microcapsules under the Ethanol Stability Test (see the data points indicated as squares and diamonds respectively). Also shown in FIG. 7A is a data point obtained following fracture of the coated PMMA microcapsules at the end of the experiment (see the data point indicated as a triangle), confirming that the liquid core material had been encapsulated. The fractured microcapsules are depicted in FIG. 7B. It can be seen from these data that the coated microcapsules exhibited negligible leakage of the liquid core material. In contrast, more than 50% of the liquid core material had leaked from the uncoated microcapsules after one day.

Example 15: Synthesis of Microcapsules Comprising a Melamine Formaldehyde Shell and a Soybean Oil Core The following procedure was used to prepare microcapsules comprising a melamine formaldehyde shell and a liquid core comprising soybean oil. Microcapsules were prepared by an in situ polymerisation process in which a butyl acrylate-acrylic acid copolymer and poly(vinyl alcohol) were used as emulsifiers.

0.9 g of butyl acrylate-acrylic acid copolymer (Colloid C351, 2% solids, Kemira), and 0.9 g of poly(acrylic acid) (PAA, 100 kDa, 35% in water Sigma) were dissolved in 20 g of Milli-Q water. An amount of sodium hydroxide was added to this solution to adjust the pH to 3.5.

0.65 g of partially methylated methylol melamine resin (Cymel 385, 80% solids, Cytec) and 20 g of hexyl salicylate were added whilst mixing at 1000 rpm for 60 minutes. In a separate container, 1.0 g of butyl acrylate-acrylic acid copolymer was mixed with 2.5 g of partially methylated methylol melamine resin in 12 g of Milli-Q water. An amount of sodium hydroxide was added to this to adjust the pH to 4.6. This was added to the main mix along with 0.4 g of sodium sulfate (Sigma). The mixture was heated to 75° C. and the temperature maintained for 6 h with continuous stirring at 400 rpm.

Example 16: Synthesis of Microcapsules Comprising a Polyacrylate Shell and a Core Comprising Soybean Oil and Isopropyl Myristate The following procedure was used to prepare microcapsules comprising a polyacrylate shell and a liquid core comprising soybean oil and isopropyl myristate. Microcapsules were prepared by an interfacial polymerisation procedure in which poly(vinyl pyrrolidone) was used as an emulsifier.

15.0 g of hexyl acetate was mixed with 3.75 g of isopropyl myristate at 400 rpm until a homogenous solution was obtained. 15.0 g of the solution was placed in a three-neck round-bottom flask and mixed at 1000 rpm using a magnetic stirrer.

The temperature was increased to 35° C., then 0.06 g of 2,2-azobis-2,4-dimethyl-pentanenitrile (Vazo-52, Du Pont) and 0.02 g of 2,2-azobis(2-methylbutyronitrile) (Vazo-67, Du Pont) were added to the reactor, with a nitrogen blanket applied at 100 $cm^3 \cdot min^{-1}$ The temperature was increased to 75° C. and held for 45 minutes before being cooled to 60° C. slowly.

The remaining oil-myristate solution was mixed with 0.05 g of t-butylaminoethyl methacrylate (Sigma), 0.04 g of 2-carboxyethyl acrylate (Sigma), and 1.95 g of hexafunctional aromatic urethane-acrylate oligomer (CN9161, Sartomer) at 400 rpm, until homogeneous. The mixture was degassed using nitrogen. At 60° C., this mixture was added to the reaction vessel and maintained at 1000 rpm at 60° C. for 10 minutes, before stirring was stopped.

2.0 g of poly(diallyl dimethyl ammonium chloride) (pDADMAC, 32% active, Sigma) was dissolved in 23.6 ml Milli-Q water. 0.11 g of 20% sodium hydroxide solution, then 0.12 g of 4,4-azobis(cyanovaleric acid) (Vazo-68 WSP, Du Pont) was added and stirred at 400 rpm until it dissolved.

The oil-monomer solution was added t to the pDADMAC solution. Mixing was then restarted at 1000 rpm for 60 minutes. The mixture was then heated slowly to 75° C. and held at this temperature for 12 h with stirring at 400 rpm.

Example 17: Preparation of Charge-Stabilised Gold Nanoparticles

The following procedure was used to prepare borohydride-stabilised gold nanoparticles.

0.34 g $HAuCl_4$ was dissolved in Milli-Q water in a 25 ml volumetric flask. 0.036 g HCl was dissolved in Milli-Q water in a 25 ml volumetric flask. The $HAuCl_4$ and HCl solutions were combined in a separate flask. 1.25 ml of this was added dropwise to 47.25 ml Milli-Q water and stirred vigorously. A borohydride solution was prepared by adding 0.095 g $NaBH_4$ dissolved in 25 ml Milli-Q water, to 0.1 g NaOH dissolved in 25 ml Milli-Q water. 1.5 ml of this was added all at once, and the solution was stirred for 1 minute. The solution changed colour from pale yellow to dark ruby red indicating formation of Au nanoparticles.

Example 18: Adsorption of Charge-Stabilised Gold Nanoparticles onto Microcapsules The following procedure was used to adsorb the charge-stabilised gold nanoparticles of Example 17 onto the surface of the microcapsules of Examples 15 and 16.

5 ml of the Au nanoparticles were added to a beaker and stirred vigorously. 2 ml microcapsules were added dropwise, and stirred vigorously for a further 10 minutes. The microcapsules were collected by centrifuging (Heraeus Megafuge R16) and removing the supernatant four times at 4000 rpm for 10 min, to remove excess nanoparticles, and were then redispersed in water (20 ml).

Example 19: Formation of Silver Film by Electroless Plating

The following procedure was used to form a continuous silver film on the microcapsules of Example 18 by electroless plating.

5 ml of microcapsules were added to a beaker containing 30 ml Milli-Q water. 0.5 ml of 0.1M $AgNO_3$ (99%, Sigma) was added and stirred vigorously. Then 50 µl of formaldehyde (35% in $H_2O$, Sigma) was added, followed by 26 µl of ammonia (25% in $H_2O$, Sigma) to control the pH to ~10, giving a silver-grey dispersion. The dispersion was then stirred for 10 min after which it was centrifuged at 4000 rpm for 10 min, 3 times, for washing, replacing the supernatant each time with Milli-Q water.

Example 20: Characterisation of Microcapsules Comprising a Melamine Formaldehyde Shell and an Au/Ag Metallic Coating Coated microcapsules comprising a melamine formaldehyde shell, a soybean oil core and a metallic coating comprising a silver film disposed on a layer of borohydride-stabilised gold nanoparticles were prepared following the procedures described in Examples 15 and 17-19. The coated microcapsules were then characterised using optical microscopy, SEM, TEM and EDX.

The coated microcapsules were then tested for their ability to retain the liquid core material using the Ethanol Stability Test described herein, and their performance was compared with that of uncoated melamine formaldehyde microcapsules. Whereas the coated microcapsules exhibited negligible leakage of the liquid core material, more than 50% of the liquid core material had leaked from the uncoated microcapsules after one day.

Example 21: Characterisation of Microcapsules Comprising a Polyacrylate Shell and an Au/Ag Metallic Coating Coated microcapsules comprising a polyacrylate shell, a core containing hexyl acetate and isopropyl myristate, and a metallic coating comprising a silver film disposed on a layer of borohydride-stabilised gold nanoparticles were prepared following the procedures described in Examples 16-19. The coated microcapsules were then characterised using optical microscopy, SEM, TEM and EDX.

The coated microcapsules were then tested for their ability to retain the liquid core material using the Ethanol Stability Test described herein, and their performance was compared with that of uncoated polyacrylate microcapsules. Whereas the coated microcapsules exhibited negligible leakage of the liquid core material, more than 50% of the liquid core material had leaked from the uncoated microcapsules after one day.

Example 22

A gold coating is placed on the surface of a melamine formaldehyde walled perfume microcapsule (MF-PMC). There are generally two steps. The first step is the addition of Pt to coat the surface of the MF-PMC. The second step is the addition of Au on the Pt coated MF-PMC surface. Lastly, scanning electron microscopy (SEM) images are provided.

The MF-PMC is generally made according to the U.S. Pat. No. 8,940,395 and available from Appleton Papers Inc. (USA). The MF-PMC is supplied as spray dried powder. Fracture strength data of these MF-PMC is 1-3 MPa as measured before being spray dried into a powder. It is not known whether spray drying impacts fracture strength. The target particle size for the MF-PMC is 18 microns (volume weighted median particle size) i.e., the largest number of MF-PMC (by volume) are at a particle size of 18 microns.

The first step is conducted either as an in situ reduction approach or as a sterically stabilized Pt nanoparticle adsorption approach. The in situ approach is described. Addition of Pt to the surface of the MF-PMC is described. 500 mg MF-PMC particles is dispersed in 20 g water and sonicated for 30 minutes to suspend particles and break up aggregates. 0.23 g $H_2PtCl_6$ is dissolved in 100 ml water. 0.076 g $NaBH_4$ is dissolved in 100 ml water. 2 mL of MF-PMC dispersion is added to 25 mL of $H_2PtCl_6$ solution and stirred for 30 mins. 25 mL of $NaBH_4$ is then added and stirred using a magnetic stirrer for a further 90 mins. The resultant suspension is centrifuged (4000 rpm for 10 mins) and washed with 25 mL distilled water. The process is repeated 2 more times.

The adsorption approach is described. Firstly, a Pt nanoparticle suspension is made. 0.23 g $H_2PtCl_6$ is dissolved in 100 mL poly(vinyl pyrrolidone) ("PVP") (1.56 uM) 0.4 mL $NaBH_4$ (0.2 M) is added and the suspension stirred at high speed for 2 minutes. The nanoparticle suspension is then left to stand overnight. Secondly, the nanoparticle suspension is added to the MF-PMC. 500 mg of the MF-PMC particles is dispersed in 20 g water and sonicated for 30 mins to suspend particles and break up aggregates. 5 mL of the Pt nanoparticle suspension is diluted with another 5 mL water. 1 mL of the MF-PMC particle suspension is added to the diluted Pt nanoparticle suspension. The combined suspensions are allowed to stir for 60 minutes on a carousel. Thereafter, the resultant suspension is centrifuged (4000 rotations per minute (rpm) for 10 minutes) and washed with 25 mL distilled water. The process is repeated 2 more times.

The second step of coating Au on Pt coated MF-PMC surface is described. This second step is the same regardless of the approach used in the first step. 1 ml of $HAuCl_4$ (40 mM), 1 ml $H_2O_2$ (60 mM) and 3 mL PVP (0.2 wt %) are added to a glass vial. 1 mL of nanoparticle coated MF-PMC are added to this and stirred on a carousel for 10 minutes. The resultant suspension is centrifuged (4000 rpm for 5 minutes) and washed with 25 mL distilled water. The process is repeated 2 more times.

Figure 8:
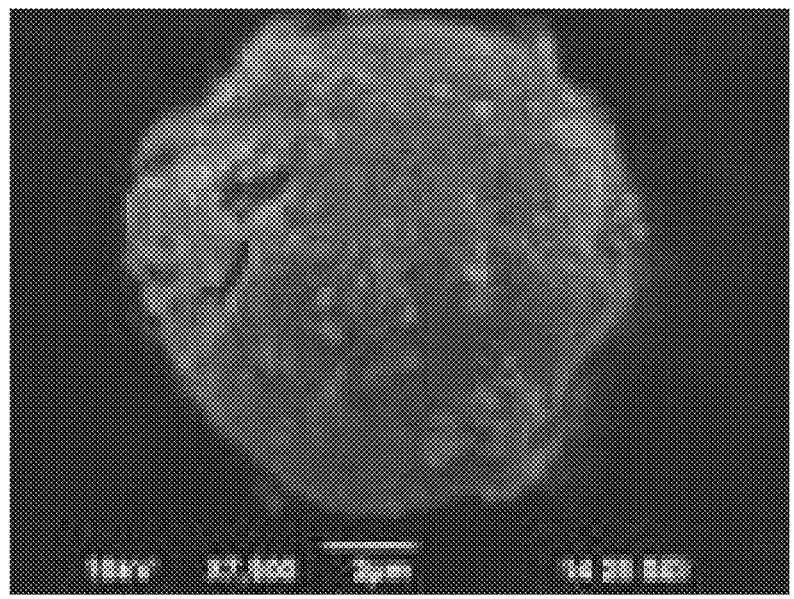
FIG. 8 is an SEM image of a melamine formaldehyde walled perfume microcapsule having a full coating of gold.
Figure 9:
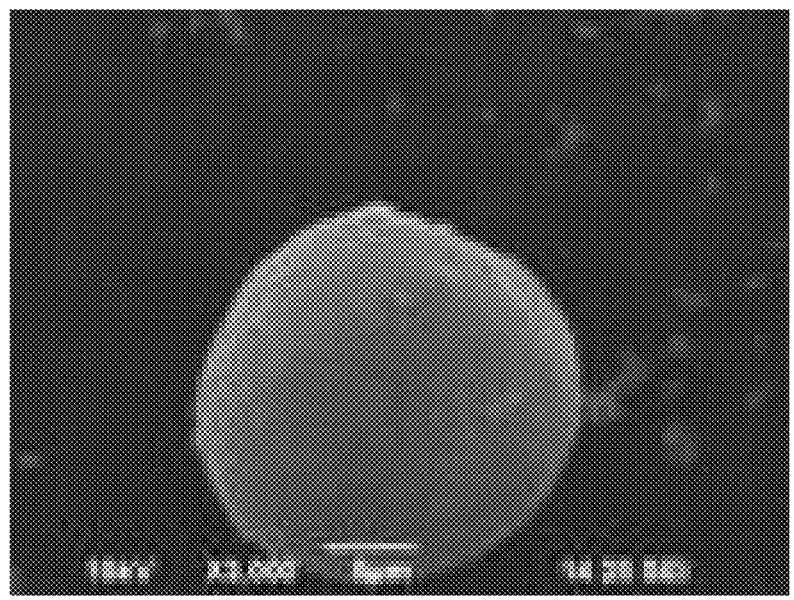
FIG. 9 is an SEM image of a melamine formaldehyde walled perfume microcapsule having a gold coating.

As can be seen in the SEM images of FIGS. 8 and 9, a gold coating is achieved for the MF-PMC. FIG. 8 is the in situ reduction approach ostensibly achieving a full coating of gold. FIG. 9 is the PVP stabilized approach where the surface of the MF-PMC achieves a gold coating.

All percentages, parts and ratios recited herein are calculated by weight unless otherwise indicated. All percentages, parts and ratios are calculated based on the total composition unless otherwise indicated. Unless otherwise noted, all component or composition levels are in reference to the active portion of that component or composition, and are exclusive of impurities, for example residual solvents or by-products which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A coated microcapsule comprising:
   a microcapsule comprising a polymeric shell and a liquid core material encapsulated therein; and
   a metallic coating surrounding said microcapsule;
   wherein the liquid core material comprises a volatile perfume oil comprising one or more volatile perfume raw materials;
   wherein the metallic coating comprises sterically stabilized nanoparticles of a first metal having a nanoparticle size of less than 100 nm adsorbed on said polymeric shell to form a discontinuous layer and a continuous film of a second metal overlaid onto the discontinuous layer by electroless plating catalyzed by the nanoparticles of the first metal;
   wherein the sterically stabilized nanoparticles of the first metal are first neutral metal nanoparticles having a surface on which are adsorbed and coated a polymeric stabilizer;
   wherein the metallic coating has a maximum thickness of 1000 nm;
   wherein the continuous film of the second metal is substantially uniform; and
   the coated microcapsules retain more than 50% by weight of the liquid core material as shown by an ethanol stability leakage test comprising combining the coated microcapsules in an aqueous solution of one part water and four parts ethanol to form a test mixture, exposing the text mixture to heat at 40° C. for seven days, thereafter separating the text mixture into the coated microcapsules and an aqueous test solution, and analyzing the aqueous test solution to determine the amount of liquid core material that has leached from the coated microcapsules.

2. A coated microcapsule according to claim 1, wherein the liquid core material comprises one or more compounds selected from isopropyl myristate, tri-esters of $C_4$-$C_{24}$ fatty acids, soybean oil, hexadecanoic acid methyl ester, isododecane, and combinations thereof.

3. A coated microcapsule according to claim 1, wherein the polymeric shell comprises a polymeric material selected from the group consisting of polyacrylates, polyethylenes, polyamides, polystyrenes, polyisoprenes, polycarbonates, polyesters, polyureas, polyurethanes, polyolefins, polysaccharides, epoxy resins, vinyl polymers, urea cross-linked with formaldehyde or gluteraldehyde, melamine cross-linked with formaldehyde, gelatin-polyphosphate coacervates optionally cross-linked with gluteraldehyde, gelatin-gum arabic coacervates, cross-linked silicone fluids, polyamines reacted with polyisocyanates, acrylate monomers polymerised via free radical polymerization, silk, wool, gelatine, cellulose, alginate, proteins, and combinations thereof.

4. A coated microcapsule according to claim 3, wherein the polymeric shell comprises a polyacrylate.

5. A coated microcapsule according to claim 4, wherein the polyacrylate is poly(methyl methacrylate) or poly(ethyl methacrylate).

6. A coated microcapsule according to claim 1, wherein the polymeric shell comprises a surface-modifying agent.

7. A coated microcapsule according to claim 6, wherein at least some of said nanoparticles are adsorbed on said surface-modifying agent.

8. A coated microcapsule according to claim 6, wherein the surface-modifying agent is selected from cetyl trimethylammonium bromide (CTAB), poly(vinyl alcohol) (PVA), poly(vinyl pyrrolidone) (PVP), and mixtures thereof.

9. A coated microcapsule according to claim 1, wherein the first metal is palladium, platinum, silver, gold, copper, nickel, tin or a combination thereof, and wherein the second metal is silver, gold, nickel, copper or a combination thereof.

10. A coated microcapsule according to claim 1, wherein the density of said nanoparticles on the polymeric shell is such that said nanoparticles cover from 0.1 to 80% of the surface area of the polymeric shell.

11. A coated microcapsule according to claim 1, wherein (i) the first metal is platinum and the second metal is gold; (ii) the first metal is gold and the second metal is silver; or (iii) the first metal is gold and the second metal is copper.

12. A coated microcapsule according to claim 1, wherein the metallic coating has a maximum thickness of 500 nm, and wherein the metallic coating has a minimum thickness of 1 nm.

13. A coated microcapsule according to claim 1, wherein the coated microcapsule has a particle size of from 0.1 micron to 500 microns.

14. A coated microcapsule according to claim 1, wherein the coated microcapsule has a fracture strength of from 0.1 MPa to 25 MPa.

15. A coated microcapsule according to claim 1, wherein:
   i) the liquid core material comprises a perfume oil comprising one or more perfume raw materials;
   ii) the polymeric shell comprises a polyacrylate, wherein the polyacrylate is selected from poly(methyl methacrylate), poly(ethyl methacrylate), or combinations thereof;
   iii) the polymeric shell further comprises a surface-modifying agent, wherein the surface-modifying agent is selected from cetyl trimethylammonium bromide (CTAB), poly(vinyl alcohol) (PVA), polyvinyl pyrrolidone) (PVP), and mixtures thereof;
   iv) (a) the first metal is platinum and the second metal is gold; (b) the first metal is gold and the second metal is silver; or (c) the first metal is gold and the second metal is copper;
   v) the metallic coating has a maximum thickness of 500 nm and a minimum thickness of 1 nm;
   vi) the coated microcapsule has a particle size of from 0.1 micron to 500 microns;
   vii) the coated microcapsule retains more than 70% by weight of the liquid core material when tested under the Ethanol Stability Test; and
   viii) the coated microcapsule has a fracture strength of from 0.1 MPa to 25 MPa.

* * * * *